US005612540A

United States Patent [19]
Richards-Kortum et al.

[11] Patent Number: 5,612,540
[45] Date of Patent: Mar. 18, 1997

[54] OPTICAL METHOD FOR THE DETECTION OF CERVICAL NEOPLASIAS USING FLUORESCENCE SPECTROSCOPY

[75] Inventors: Rebecca Richards-Kortum, Austin; Gregg Staerkel, Houston; Youseph Yazdi, Austin; Michele F. Mitchell, Houston, all of Tex.

[73] Assignee: Board of Regents, The University of Texas Systems, Austin, Tex.

[21] Appl. No.: 412,325

[22] Filed: Mar. 31, 1995

[51] Int. Cl.$^6$ ........................................ G01N 21/64
[52] U.S. Cl. ............................ 250/461.2; 250/459.1
[58] Field of Search ........................... 250/459.1, 461.2

[56] References Cited

U.S. PATENT DOCUMENTS

| | | |
|---|---|---|
| 4,786,813 | 11/1988 | Svanberg et al. . |
| 4,930,516 | 6/1990 | Alfano et al. . |
| 5,042,494 | 8/1991 | Alfano . |
| 5,046,501 | 9/1991 | Crilly . |
| 5,115,137 | 5/1992 | Andersson-Engels et al. . |
| 5,125,404 | 6/1992 | Kittrell . |
| 5,131,398 | 7/1992 | Alfano et al. . |
| 5,168,162 | 12/1992 | Oong et al. . |
| 5,174,297 | 12/1992 | Dalkuzono . |
| 5,201,318 | 4/1993 | Rava et al. . |
| 5,261,410 | 11/1993 | Alfano et al. . |
| 5,303,026 | 4/1994 | Strobl et al. . |
| 5,318,024 | 6/1994 | Kittrell et al. . |
| 5,348,018 | 9/1994 | Alfano et al. . |
| 5,408,996 | 4/1995 | Salb . |
| 5,421,339 | 6/1995 | Ramanujam et al. . |

FOREIGN PATENT DOCUMENTS 9000035   1/1990   WIPO ........................ 250/459.1

OTHER PUBLICATIONS

W. Glassman, "Ultraviolet Excited Fluorescent Spectra from Non–Malignant and Malignant Tissues of the Gynecological Tract," *Lasers in the Lifesciences*, 49–58, 1992.

W. Lohmann et al., "Native Fluorescence of the Cervix Uteri as a Marker for Dysplasia and Invasive Carcinoma," *European Journal of Obstetrics & Gynecology and Reproductive Biology*, 31:249–253, 1989.

N. Ramanujam et al., "Diagnosis of Cervical Intraepithelial Neoplasia Using Laser–Induced Fluorescence," *Poster Presentation at Future Directions of Lasers in Surgery and Medicine III*, 1993.

R. Walpole and R. Myers, *Tests of Hypotheses, In: Probability and Statistics for Engineers and Scientists*, 2nd Ed., Chapter 7:v, 238–259, 1978.

W. Dillon and M. Goldstein, *Principal Components Analysis, In: Multivariate Analysis, Methods and Applications*, Chapter 2:23–392, 1984.

C. Liu et al., "Raman Fluorescence, and Time–Resolved Light Scattering as Optical Diagnostic Techniques to Separate Diseased and Normal Biomedical Media," *J Photochem. Photobiol. B Biol.*, 16:187–209, 1992.

D. Redd et al., "Raman Spectroscopic Characterization of Human Breast Tissues: Implications for Breast Cancer Diagnosis," *Applied Spectroscopy*, 47(6):787–791, 1993.

R. Alfano et al., "Human Breast Tissues Studied by IR Fourier Transform Raman Spectroscopy," *Lasers in the Life Sciences*, 4(1):23–28, 1991.

G. Small et al., "Strategies for Coupling Digital Filtering with Partial Least–Squares Regression: Application to the Determinationof Glucose in Plasma by Fourier Transform Near–Infrared Spectroscopy," *Anal. Chem.*, 65:3279–3289, 1993.

(List continued on next page.)

*Primary Examiner*—Carolyn E. Fields
*Assistant Examiner*—Edward J. Glick
*Attorney, Agent, or Firm*—Arnold, White & Durkee

[57] ABSTRACT

A method for detecting tissue abnormality, particularly precancerous cervical tissue, through fluorescence spectroscopy is disclosed. In vitro fluorescence measurements over a variety of different fluorescence spectra are used to screen tissue samples. Using a principal component analysis (PCA), it is possible to discriminate between normal and dysplastic tissues with relatively low false-positive and false-negative results.

15 Claims, 9 Drawing Sheets

OTHER PUBLICATIONS

K. Schomacker et al., "Ultraviolet Lasers–Induced Fluorescence of Colonic Tissue: Basic Biology and Diagnostic Potential," *Lasers in Surgery and Medicine*, 12:63–78, 1992.

R. Cothren et al., "Gastrointestinal Tissue Diagnosis by Laser–Induced Fluorescence Spectroscopy at Endoscopy," *Gastrointestinal Endoscopy*, 36:105–111, 1990.

S. Andersson–Engels et al., "Fluorescence Imaging and Points Measurements of Tissue: Applications to the Demarcation of Malignant Tumors and Atherosclerotic Lesions from Normal Tissue," *Photochemistry and Photobiology*, 53:807–814, 1991.

R. Rava et al., "Early Detection of Dysplasia in Colon and Bladder Tissue Using Laser–Induced Fluorescence," *SPIE, Optical Methods for Tumor Treatment and Early Diagnosis: Mechanisms and Techniques*, 1426:68–78, 1991.

R. Cothren et al., "Argon Ion Laser–Induced Tissue Fluorescence: Clinical Spectroscopic Studies," *SPIE, Optical Fibers in Medicine III*, vol. 906, Abstract only, 1988.

S. Lam et al., "Detection of Dysplasia and Carcinoma In Situ by Ratio Fluorometry," *Am. Rev. Respir. Dis.*, 146:1458–1461, 1992.

R.R. Alfano et al., "Optical Spectroscopic Diagnosis of Cancer in Normal Breast Tissues," *J. Opt. Soc. Am. B.*, 6:1015–1023, May 1989.

R.R. Alfano et al., "Fluorescence Spectra from Cancerous and Normal Human Breast and Lung Tissues," *IEEE Journal of Quantum Electronics*, QE–23:1806–1811, Oct. 1987.

J. Hung et al., "Autofluorescence of Normal and Malignant Bronchial Tissue," *Lasers in Surgery and Medicine*, 11:99–105, 1991.

R. Richards–Kortum et al., "Spectroscopic Diagnosis of Colonic Dysplasia," *Photochemistry and Photobiology*, 53:777–786, 1991.

C. Kapadia et al., "Laser–Induced Spectroscopy of Human Colonic Mucosa: Detection of Adenomatous Transformation," *Gastroenterology*, 99:150–157, 1990.

P. Wong et al., "Infrared Spectroscopy of Exfoliated Human Cervical Cells: Evidence of Extensive Structural Changes During Carcinogensis," *Proc. Natl. Acad. Sci. USA*, 88:10988–10992, 1991.

OPTICAL METHOD FOR THE DETECTION OF CERVICAL NEOPLASIAS USING FLUORESCENCE SPECTROSCOPY

BACKGROUND OF THE INVENTION

The field of the invention relates to optical methods used for the screening and diagnosis of tissue abnormalities. In particular, the invention relates to the use of fluorescent spectroscopy to detect cancerous and precancerous tissues of the cervix.

Cervical cancer is the second most common malignancy in women worldwide, exceeded only by breast cancer and in the United States, it is the third most common neoplasm of the female genital tract—15,000 new cases of invasive cervical cancer and 55,000 cases of carcinoma in situ (CIS) were reported in the U.S. in 1994. In 1994, an estimated 4,600 deaths occurred in the United States alone from cervical cancer. However, in recent years, the incidence of pre-invasive squamous carcinoma of the cervix has risen dramatically, especially among young women. Women under the age of 35 years account for up to 24.5% of patients with invasive cervical cancer, and the incidence is continuing to increase for women in this age group. It has been estimated that the mortality of cervical cancer may rise by 20% in the next decade unless further improvements are made in detection techniques.

The mortality associated with cervical cancer can be reduced if this disease is detected at the early stages of development or at the pre-cancerous state (cervical intraepithelial neoplasia (CIN)). A Pap smear is used to screen for CIN and cervical cancer in the general female population. This technique has a false-negative error rate of 15–40%. Am abnormal Pap smear is followed by colposcopic examination, biopsy and histologic confirmation of the clinical diagnosis. Colposcopy requires extensive training and its accuracy for diagnosis is variable and limited even in expert hands. A diagnostic method that could improve the performance of colposcopy in the hands of less experienced practitioners, eliminate the need for multiple biopsies and allow more effective wide scale diagnosis could potentially reduce the mortality associated with cervical cancer.

Recently, fluorescence, infrared absorption and Raman spectroscopies have been proposed for cancer and precancer diagnosis. Many groups have successfully demonstrated their use in various organ systems. Auto- and dye-induced fluorescence have shown promise in recognizing atherosclerosis and various types of cancers and precancers. Many groups have demonstrated that autofluorescence may be used for differentiation of normal and abnormal tissues in the human breast and lung, bronchus and gastrointestinal tract. Fluorescence spectroscopic techniques have also been investigated for improved detection of cervical dysplasia.

Despite these advances, there remains a need for diagnostic methods with improved accuracy and ease of application that also provide more rapid results. Such methods will permit earlier diagnosis, more effective patient management and, potentially, reduce mortality.

SUMMARY OF THE INVENTION

Thus, it is an objective of the present invention to provide improved methods for the early detection of neoplasia. In particular, it is an objective of the present invention to provide improved spectroscopic methods for the identification of abnormal cervical tissue, thereby providing a rapid, accurate and simple method for detecting cancerous or precancerous cervical tissue.

In satisfying these and other objectives, there is provided a method for the optical diagnosis of tissue abnormalities. In one embodiment, the present invention provides for the detection of tissue abnormality in a tissue sample in vitro by illuminating a tissue sample with a series of electromagnetic radiation wavelengths selected to cause the tissue sample to produce a series of fluorescence intensity spectra indicative of tissue abnormality. The fluorescence intensity spectra emitted from the tissue sample as a result of illumination with the electromagnetic radiation are detected. Then, a probability that the tissue sample is normal or abnormal is calculated from the fluorescence intensity spectra.

The invention further contemplates that the calculations include principal component analysis of the spectra, relative to a plurality of preprocessed spectra obtained from tissue samples of known diagnosis. The invention also contemplates normalizing the spectra, relative to a maximum intensity within the spectra, and mean-scaling the spectra as a function of a mean intensity of the spectra.

The apparatus of the present invention includes a controllable illumination device for emitting a plurality of electromagnetic radiation wavelengths selected to cause a tissue sample to produce a fluorescence intensity spectrum indicative of tissue abnormality, an optical system for applying the plurality of radiation wavelengths to a tissue sample, a fluorescence intensity spectrum detecting device for detecting an intensity of fluorescence spectra emitted by the sample as a result of illumination by the plurality of electromagnetic radiation wavelengths, a data processor, connected to the detecting device, for analyzing detected fluorescence spectra to calculate a probability that the sample is abnormal.

These and other features and advantages of the present invention will become apparent to those of ordinary skill in this art with reference to the appended drawings and following detailed description.

DETAILED DESCRIPTION

I. Introduction

Figure 1:
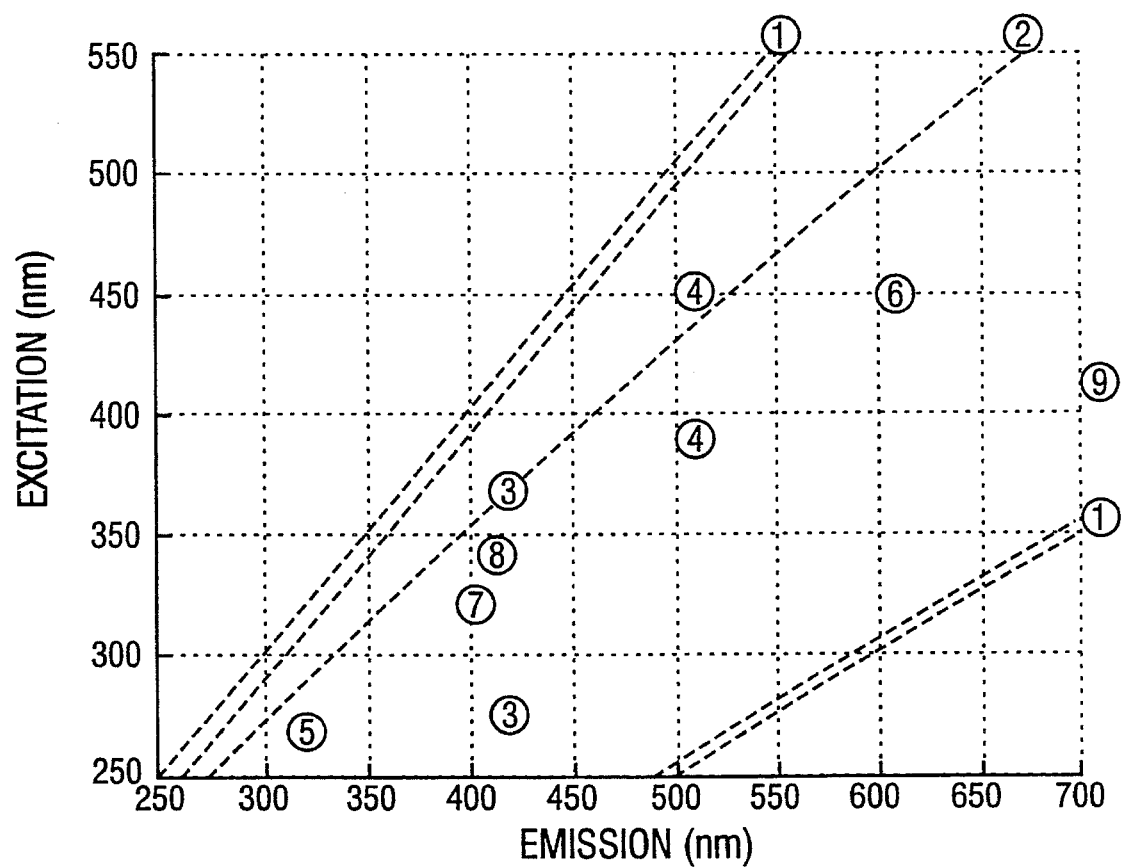
FIG. 1 is a graph of the λex/λem values for known cell and tissue flurophores.

Clinical detection of neoplasias can be divided into two different kinds of analysis. First, screening provides a way to identify suspicious samples taken from a rather large pool of subjects. Subjects may be from the population as a whole or they may be part of a group identified as having a higher than average risk for one or more cancers. It is desirable that, because of the sheer number of tests, screening assays be relatively rapid, easy to conduct and inexpensive. It also is desirable that they exhibit a low false-negative rate.

Once patients have been screened, it is necessary to proceed with more detailed testing that can be referred to generically as diagnosis. In diagnosis, the neoplasias nature of the sample is confirmed and, in addition, further information on the type and degree of dysplasia is obtained. This provides the clinician with an understanding of the disease state necessary to begin a treatment regimen. For diagnosis, cost, ease of application and rapidity are less important, though always desirable. It is important, however, that diagnostic procedures be accurate with respect to the kind of cancer identified and its clinical stage.

The present invention is an example of the first kind of detection, screening. Present screening methods, like Pap smears, are time intensive, require highly trained individuals and are relatively expensive. Even so, the subjective nature of the scoring often results in an unacceptable number of false negatives, the outcome of which can be devastating. It is believed that by using a more objective standard like fluorescent emissions, the accuracy of the screen can be improved. In addition, the possibility for automation has further benefits in terms of time and expense.

A. Method for Determining Fluorescent Spectra

The present invention is premised on the hypothesis that normal and abnormal cells will emit differing fluorescent spectra in response to stimulating electromagnetic radiation. In its most general form, the methods comprises providing a tissue sample, illuminating that tissue sample with electromagnetic radiation, detecting fluorescence of the sample and comparing the fluorescence of the sample with that of some standard. Each of these steps is described in greater detail, below.

Obtaining a tissue sample can be achieved by any one of a variety of different means, largely depending on the nature of the sample to examined. For example, for examination of solid tissues, samples can be taken by biopsy. Alternatively, scrapings of cells can be taken from the tissue of interest. For examination of cells that are not part of solid tissue, liquid samples may be obtained and the cells isolated therefrom. For example, blood samples may be obtained by any normal methodology. Aspiration of fluids also is contemplated, such as thin tissue aspirates.

Once obtained, it may be necessary to further process the samples before they are examined. Further processing may include various forms of physical arrangement of the samples. For example, with solid tissues, it may be necessary to prepare thin sections. It also may be desired to dissociate the cells from each other and disperse them as a thin film monolayer. Dissociation may be accomplished by physical or enzymatic means. Similarly, dissociated cells in fluid samples or in scrapings may be concentrated and dispersed in a monolayer. In other instances, it may be desirable to concentrate disperse cells as a pellet. This can be accomplished by centrifugation of the liquid samples.

Further pre-illumination processing includes chemical treatments such as fixation steps. In some cases, it will be desirable that the natural autofluorescence of the sample be unaffected. In such a case, the chemical treatment is selected so that the fluorescent species are not altered. In other cases, it may prove useful to use treatments that cause different autofluorescent profiles. Exemplary treatments include alcohol fixation. Suitable alcohols include methanol, ethanol, propanol, isopropanol, n-butanol and t-butanol.

Typically, the samples are provided on a surface, though they can be provided in an open or closed container. A typical surface is a glass or quartz microscope slide. With certain surfaces, such as glass slides, there may be variation from item to item, requiring internal recalibration with each sample. There also may be distorting effects, especially for container-enclosed samples, that must be taken into account.

Once the samples are prepared, the illumination is effected. In the present invention, a variety of different wavelengths can be used spanning from about 200 nm to over 700 nm. Under most circumstances, a plurality of different wavelengths will be applied, individually, to a single sample. Generally, the greater the number of wavelengths used, the better the ability to discriminate between physiologically distinct tissue samples. Of course, at some point, the intervals between wavelengths will be so small that the information achieved will become redundant. Those of skill in the art, knowing the fluorescent behavior of biological molecules, will be able to select both the appropriate number and range of wavelengths for a given purpose.

In one embodiment, wavelengths from 250 nm to 550 nm were applied, with 10 nm intervals. Thus, 31 different wavelengths were applied to a single sample in sequence. Because a series of different illuminations and emissions are required, it is important that the sample not be affected by the illuminating wavelengths. One such effect would be photobleaching, which has been shown to be significant in arterial tissue above excitation fluences of 80 mJ/mm$^2$.

Figure 2:
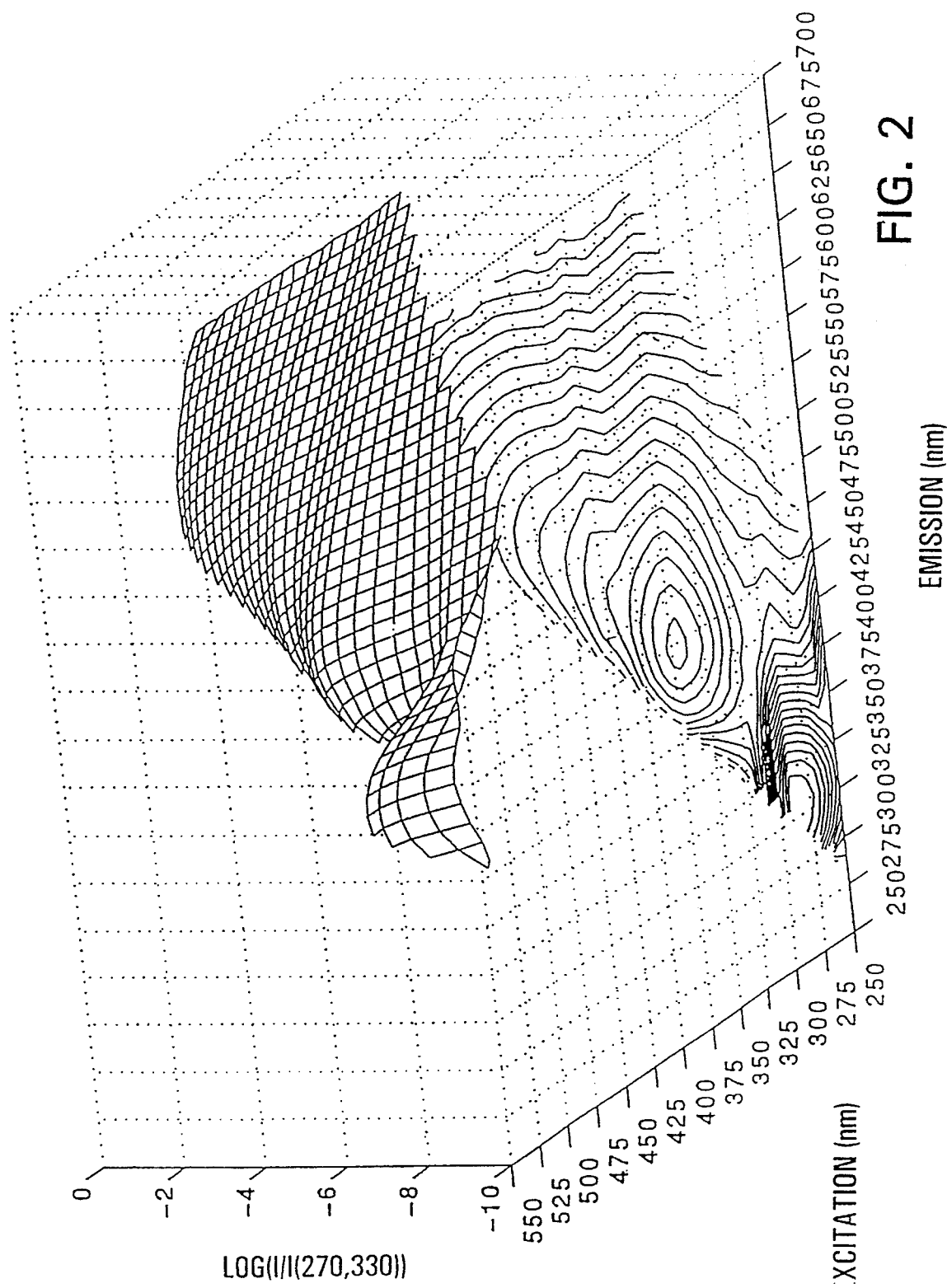
FIG. 2 is a graph of the average cell pellet EEM.
Figure 3:
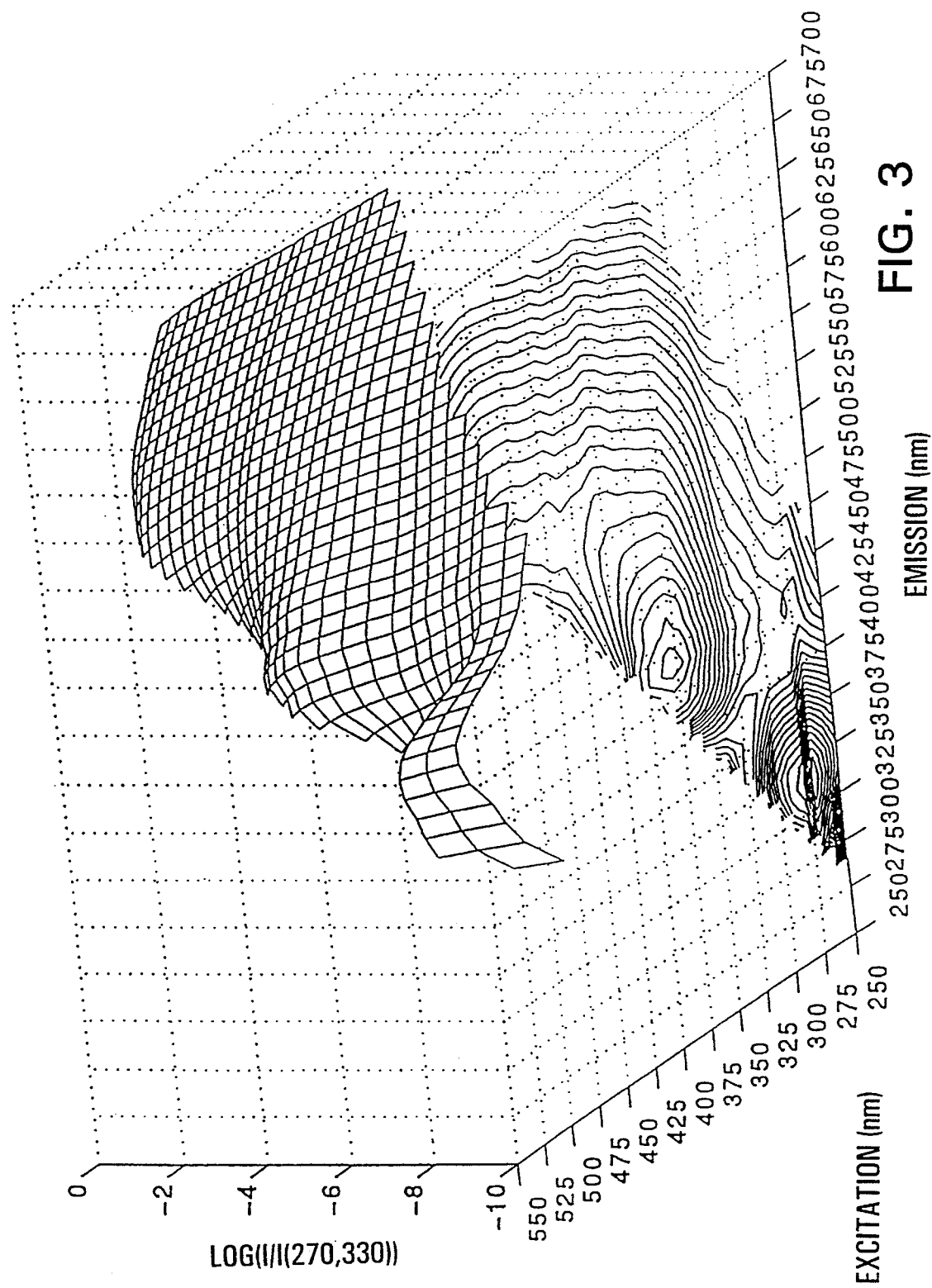
FIG. 3 is a graph of a sample cell pellet EEM with a high (430,520) peak.
Figure 4:
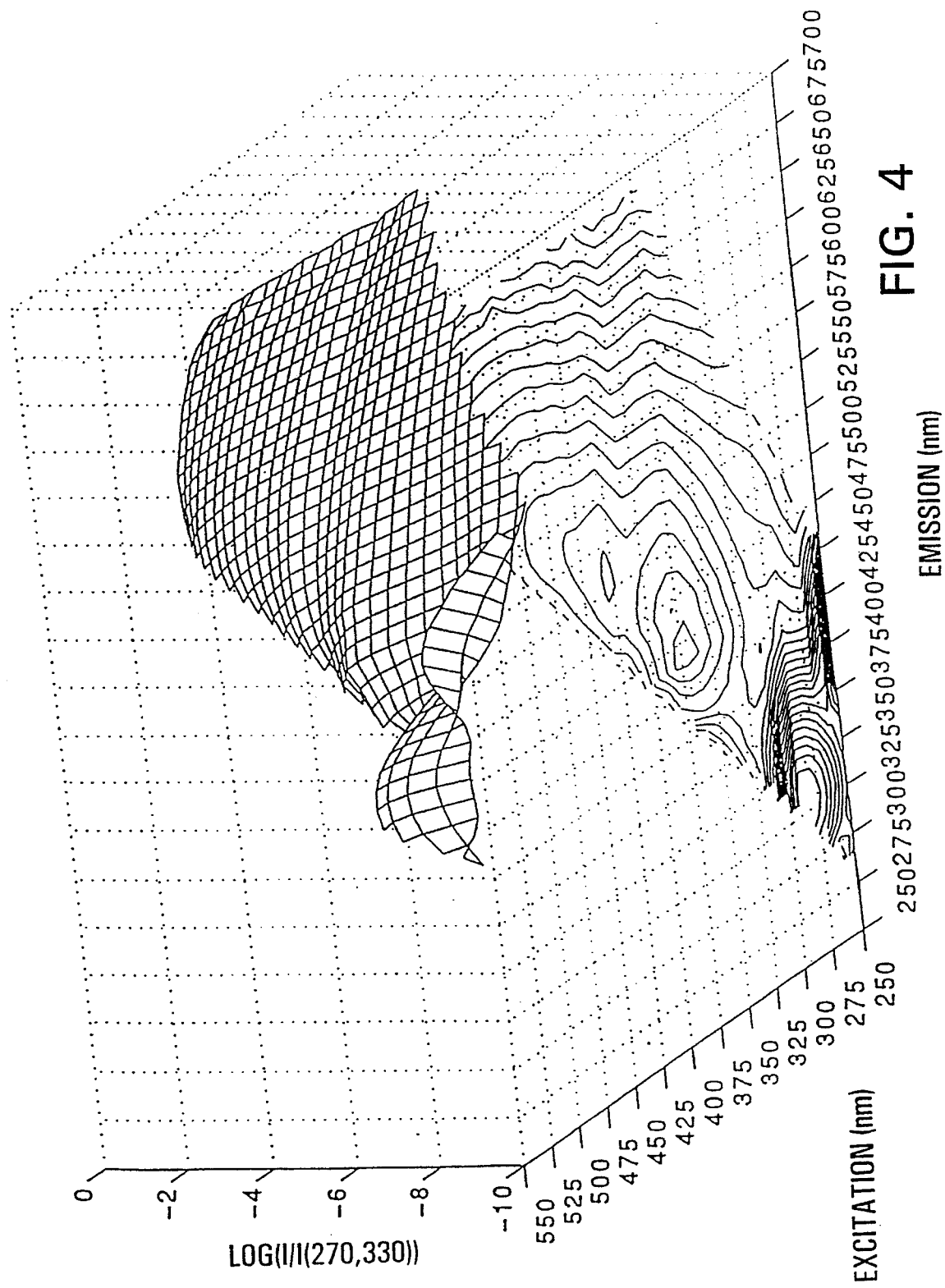
FIG. 4 is a graph of a sample cell pellet EEM with a high (250,400) peak.

The next step in the method is detection. For each illuminating wavelength, an emission spectrum is determined over a range of wavelengths. Again, a series of wavelengths may be used with the greater number examined, the more information with which to detect differences between normal and abnormal tissues. The emission spectra are normalized to an appropriate $\lambda$ex/$\lambda$em. The excitation-emission matrices (EEM's) may be plotted three dimensionally, with excitation wavelength, emission wavelength and log(1/1($\lambda$ex/$\lambda$em)) as the three axes. FIGS. 2–4 depict various EEM's.

In another embodiment, emissions were monitored from 250 nm to 700 nm at 10 nm intervals. Thus, the spectra comprises 46 different emission readings. These readings were normalized to an $\lambda$ex/$\lambda$em of (270,330). Based on the results discussed below, it appears that individual wavelengths do not adequately discriminate between normal and abnormal tissues. Taken as a group, however, there appears to be a correlation between fluorescence values and pathology. In order to maximize this correlation, various statistical manipulations were applied to the data, as discussed in detail below.

FIG. 1 is a graph showing the excitation/emission profiles for various known cell and tissue fluorophores. Those of skill in the art are aware of other potential natural fluorophores whose fluorescence may be used to generate emission spectra which may then be used in accordance with the present invention.

B. Multi-Variate Statistical Method Development

In order to maximize the correlation between fluorescence values and the physiologic state of the sample tissue, multivariate statistics were applied. The five primary steps involved in the multivariate statistical method are 1) preprocessing of spectral data from each patient to account for interpatient variation, 2) dimension reduction of the preprocessed spectra in the calibration set using principal component analysis, 3) selection of the diagnostically most useful principal components using a two-sided unpaired t-test and other criteria and 4) development of an optimal classification scheme based on Fisher's discriminant analysis using the diagnostically useful principal component scores of the calibration set as inputs with cross-validation. These five individual steps of the multivariate statistical method are presented below in more detail.

1) Preprocessing: The objective of preprocessing is to calibrate tissue spectra for inter-patient variation which might obscure differences in the spectra of different tissue types. A normalization method of preprocessing was invoked on the spectral data.

Spectra were normalized by dividing the fluorescence intensity at each emission wavelength by the fluorescence intensity at (280 nm, 330 nm) of that sample. Normalizing a fluorescence spectrum removes absolute intensity information; methods developed from normalized fluorescence spectra rely on differences in spectral line shape information for diagnosis.

2) Principal Component Analysis: Principal component analysis (PCA) is a linear model which transforms the original variables of a fluorescence emission spectrum into a smaller set of linear combinations of the original variables called principal components that account for most of the variance of the original data set. Principal component analysis is described in Dillon W. R., Goldstein M., *Multivariate Analysis: Methods and Applications*, John Wiley and Sons, 1984, pp. 23–52, the disclosure of which is expressly incorporated herein by reference. While PCA may not provide direct insight to the morphologic and biochemical basis of tissue spectra, it provides a novel approach of condensing all the spectral information into a few manageable components, with minimal information loss. Furthermore, each principal component can be easily related to the original emission spectrum, thus providing insight into diagnostically useful emission variables.

Prior to PCA, a data matrix is created where each row of the matrix contains the concatenated preprocessed fluorescence spectra of a sample and each column contains the pre-processed fluorescence intensity at each excitation-emission wavelength pair. The data matrix D (r×c), consisting of r rows (corresponding to r total samples from all patients in the training set) and c columns (corresponding to intensity at c emission-excitation wavelength pairs) can be written as:

$$D = \begin{pmatrix} D_{11} & D_{12} & \ldots & D_{1c} \\ D_{21} & D_{22} & \ldots & D_{2c} \\ D_{r1} & D_{r2} & \ldots & D_{rc} \end{pmatrix} \quad (1)$$

The first step in PCA is to calculate the covariance matrix, Z. First, each column of the preprocessed data matrix D is mean-scaled. The mean-scaled preprocessed data matrix, $D_m$ is then multiplied by its transpose and each element of the resulting square matrix is divided by (r−1), where r is the total number of samples. The equation for calculating Z is defined as:

$$Z = \frac{1}{r-1} (D_m/D_m) \quad (2)$$

The square covariance matrix, Z (c×c) is decomposed into its respective eigenvalues and eigenvectors. Because of experimental error, the total number of eigenvalues will always equal the total number of columns (c) in the data matrix D assuming that c<r. The goal is to select n<c eigenvalues that can describe most of the variance of the original data matrix to within experimental error. The variance, V, accounted for by the first n eigenvalues can be calculated as follows:

$$V = 100 \left( \frac{\sum_{j=1}^{n} \lambda_j}{\sum_{j=1}^{c} \lambda_j} \right) \quad (3)$$

The criterion used in this analysis was to retain the first n eigenvalues and corresponding eigenvectors that account for 99.9% of the variance in the original data set.

Next, the principal component score matrix can be calculated according to the following equation:

$$R = D\, C \quad (4)$$

where, D (r×c) is the preprocessed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal to each other.

Finally, the component loading is calculated for each principal component. The component loading represents the correlation between the principal component and the variables of the original fluorescence emission spectrum. The component loading can be calculated as shown below:

$$CL_{ij} = \frac{C_{ij}}{\sqrt{S_{ii}}} \sqrt{\lambda_j} \quad (5)$$

where, $CL_{ij}$ represents the correlation between the ith variable (preprocessed intensity at ith emission wavelength) and the jth principal component. $C_{ij}$ is the ith component of the jth eigenvector, $\lambda_j$ is the jth eigenvalue and $S_{ii}$ is the variance of the ith variable.

Principal component analysis was performed on each type of preprocessed data matrix, described above. Eigenvalues accounting for 99.9% of the variance in the original preprocessed data set were retained The corresponding eigenvectors were then multiplied by the original data matrix to obtain the principal component score matrix R.

3) Student's T-Test: Average values of principal component scores were calculated for each histopathologic tissue category for each principal component obtained from the preprocessed data matrix. A two-sided unpaired student's t-test was employed to determine the diagnostic contribution of each principal component. Such a test is disclosed in Derore J. L., *Probability and Statistics for Engineering and the Sciences*, Brooks/Cole, 1992, and in Walpole R. E., Myers R. H., *Probability and Statistics for Engineers and Scientists*, Macmillan Publishing Co., 1978, Chapter 7, the disclosures of which are expressly incorporated herein by reference. The hypothesis that the means of the principal component scores of two tissue categories are different were tested for normal smears and abnormal smears (ASCUS, LGSIL, HGSIL). Principal components were ranked in order of increasing p value. Fisher's discriminant analysis was performed using the most significant principal components and method performance was evaluated. Principal components were then added one at a time and Fisher's discriminant analysis was again performed. This process was repeated until no further improvement was reached or a decrease in performance was noted. Principal components chosen in this manner were used in the diagnostic method.

4) Logistic Discrimination: Logistic discriminant analysis is a statistical technique that may be used to develop diagnostic methods based on posterior probabilities, overcoming the drawback of the binary decision scheme employed in the two-stage method. This statistical classification method is based on Bayes theorem and may be used to calculate the posterior probability that an unknown sample belongs to each of the possible tissue categories identified. Logistic discrimination is discussed in Albert A., Harris E. K., *Multivariate Interpretation of Clinical Laboratory Data*, Marcel Dekker, 1987, the disclosure of which is expressly incorporated herein by reference. Classifying the unknown sample into the tissue category for which its posterior probability is highest results in a classification scheme that minimizes the rate of misclassification.

For two diagnostic categories, $G_1$ and $G_2$, the posterior probability of being a member of $G_1$, given measurement x, according to Bayes theorem is:

$$P(G_1|X) = \frac{P(x|G_1)P(G_1)C(2|1)}{P(x|G_1)P(G_1)C(2|1) + P(x|G_2)P(G_2)C(1|2)} \quad (6)$$

where $P(x|G_i)$ is the conditional joint probability that a tissue sample of type i will have principal component score x, and $P(G_i)$ is the prior probability of finding tissue type i in the sample population. $C(j|i)$ is the cost of misclassifying a sample into group j when the actual membership is group i.

The prior probability $P(G_i)$ is an estimate of the likelihood that a sample of type i belongs to a particular group when no information about it is available. If the sample is considered representative of the population, the observed proportions of cases in each group can serve as estimates of the prior probabilities. In a clinical setting, either historical incidence figures appropriate for the patient population can be used to generate prior probabilities, or the practitioner's colposcopic assessment of the likelihood of precancer can be used to estimate prior probabilities, as is known in the art.

The conditional probabilities may be developed from the probability distributions of the n principal component scores for each tissue type, i. The probability distributions may be modeled using the gamma function, which is characterized by two parameters, alpha and beta, which are related to the mean and standard deviation of the data set. The normal function is typically used to model probability distributions and is defined below:

$$f(x) = (1/(\sqrt{2\pi})\Sigma)e^{-(x-m)/(\sqrt{2})\Sigma} \quad (7)$$

The normal distribution function may be used to calculate the conditional probability that a sample from tissue type i, will exhibit the principal component score, x. If more than one principal component is needed to describe a sample population, then the conditional joint probability is simply the product of the conditional probabilities of each principal component (assuming that each principal component is an independent variable) for that sample population.

Fisher's discriminant analysis is a particular statistical technique for classifying individuals or objects in to mutually exclusive and exhaustive groups on the basis of a set of independent variables. In this particular application of Fisher's method, the objects are N patient cytological samples, the groups are the diagnostic classifications (normal versus abnormal) and the P variables are the principal components X derived from the fluorescence spectra of the samples.

Fisher's method calculates a score Y for each of the samples, based on a linear combination of the variables, i.e., $$Y(N) = b_1 * X_1 * (N) + b_2 * X_2 * (N) + \ldots + b_p * X_p(N)$$

The coefficients $b_1$ through $b_p$ are calculated so that the difference between the scores for the normals and the abnormals is maximized. Assuming that the X is normally distributed for the two groups, and assuming that the covariance s of X is the same for the two groups, then the best choice for $b_1$ is $$b1 = s^{-1}*(\text{avg. of } x_1 \text{ of norm.} - \text{avg. of } x_1 \text{ for abnorm.})$$

and similarly for $b_2$ through $b_p$. Then, a cutoff value for Y is selected and all samples with scores above the threshold are classified as belonging to the first group, normals, and samples with scores below the threshold are classified as belonging to the second group, abnormals. Since there is overlap in the distributions of Y for the two groups, some samples will be misclassified no matter where the cutoff is chosen. The cutoff is chosen to be the one that results in the lowest misclassification rate. The cutoff value given the above assumptions is $$Y_c = (n_2 Y_1 + n_1 Y_2)/(n_1 + n_2)$$

where $n_1$ is the number of samples in group 1, and $Y_1$ is the Y score using the average values of the X variables for group 1, likewise for group 2. $Y_c$ can be adjusted from this value to reduce the FN rate at the expense of the FP rate, or vice versa, depending on the application.

Since both the b and Yc values are calculated from the data, it may be asked how well this method will classify new samples, whose values for X were not used in the above-calculations. This performance can be estimated by using cross-validation techniques. For each sample, b and Yc are calculated using the other sample data, and then the method is used to classify that sample. The misclassification error rate for all samples is measured this way is taken as an unbiased estimate of what one can expect when using Fisher's discriminate analysis to classify new samples. Dillon and Goldstein (1985).

II. Examples

In order to evaluate the neoplastic diagnostic potential of cellular autofluorescence, excitation of exfoliated, ethanol-fixed cervical squamous epithelial cells with a plurality of wavelengths was performed. In addition, the effects on the fluorescent spectra of different specimen preparation methods were examined using both cell pellet and monolayer preparations made from the same samples.

A. Sample Preparation

Exfoliated cervical cells were obtained from patients referred to MD Anderson Cancer Center for routine screening, as well as colposcopy, on the basis of previous abnormal cervical cytology. Conventional Pap smears were obtained and the normally discarded cells remaining on the swab suspended in an ethanol-based fixative (PreservCyt Solution, Cytyc Corp., Marlborough, Mass.). From each suspension, two types of samples were prepared. First, a monolayer cell touch prep was prepared onto an ordinary glass microscope slide using the CYTYC Thinprep device (Hutchinson, 1992). This device extracts an aliquot from the suspension and filters it to remove red blood cells and other debris smaller and larger than epithelial cells. The cells were deposited in an circular area 20 mm in diameter.

The remaining cells in suspension were centrifuged and resuspended three times in HPLC-grade ethanol to remove the fluorescent preservative solution. The number of cells in suspension was determined using a hemocytometer and found to vary between $1-50 \times 10^4$ cells. The cells were then spun down to a pellet, placed on a spot approximately 3 mm in diameter on a quartz microscope slide and air dried.

B. Fluorescent Spectroscopy Apparatus and Conditions

All fluorescence measurements were made using a standard scanning fluorimeter (SPEX, Fluorclog II, Edison, N.J.) with a spectral resolution of 5 nm FWHM. Beam area was approximately 2 mm$^2$. Slides were placed so that the cells were on the side facing the beam, and the beam was focused onto this surface of the slide. Excitation light was incident normally and emission was collected at an angle of 20 degrees from the normal. The signal at each ($\lambda$ex,$\lambda$em) value was integrated for 2 seconds. Data were corrected for the non-uniform spectral response of the emission monochromator and detector using correction factors supplied with the instrument. Also, spectra were corrected for variability with wavelength in the intensity of the excitation source using a Rhodamine B quantum counter (20).

Fluorescence excitation-emission matrices (EEM's) were recorded for each cell pellet sample. Excitation wavelengths ranged from 250 to 550 nm, in 10 nm increments, and emission was measured from 10 nm above the excitation wavelength to 10 nm below the 2nd harmonic of the excitation wavelength, up to 700 nm, in 10 nm increments. A background EEM was recorded from a quartz slide containing supernatant only from the resuspension of one sample. This background EEM was subtracted from each pellet EEM. For several samples, a second emission spectrum was recorded at 250 nm excitation after the initial EEM to check for photobleaching effects. All EEMs were normalized with respect to the intensity at (270,330).

For the ThinPrep samples, one excitation spectrum from 350 nm to 410 nm at 440 nm emission was recorded, and two emission spectra were recorded, at excitations of 280 nm and 370 nm, using the same increments and spectral ranges as the EEMs above. Since the UV fluorescence of the glass slides differed between slides, a background spectrum was recorded from each slide from a region with no cells. All spectra were normalized with respect to the intensity at (280,330).

C. Pap Smears

Conventional Pap smears were read by staff cytopathologists at M. D. Anderson Cancer Center. Diagnosis was done using the standard diagnostic classifications, where the samples are classified as Normal, HPV, CIN I (mild dysplasia), CIN II (moderate dysplasia), or CIN III (severe dysplasia or carcinoma in situ), and Squamous Carcinoma (Vooijs, 1991).

Samples were obtained from 80 patients, of which 36 were not used due to inconclusive diagnoses, samples too dilute, contamination with blood or other foreign matter such as cotton from swabs used in the sample collection, or errors made in the data collection. Of the remaining 44 samples, 15 had conventional Pap smears which were diagnosed as normal (negative for malignant cells) and 29 were read as abnormal (HPV - 14; CINI -9; CINII - 10; CINIII - 10). The ages ranged from 20 to 52, with the average age of 33. There were 21 whites, 7 hispanics, 15 blacks, and 1 oriental. For comparison of the pellet to the ThinPrep preparations, 23 samples were selected from the patients mentioned above, of which 10 were normal and 13 abnormal.

D. Fixed Cell Fluorescence

FIG. 2 is a graph of the average EEM for all 44 pellet prepared samples used. All plots are normalized to the (270,330) values and plotted on a log scale. Contour plot lines are spaced evenly also on a log scale. The most intense fluorescence peak is at (280,330), characteristic of tryptophan. A peak also is present at (370,450), and a slight shoulder at (280,450), both characteristic of PN. A shoulder is also present at (250,400), due to contaminants of unknown origin. There is a slight shoulder near (430,520) due to flavoprotein as well as a valley in the excitation spectra corresponding to the Soret Hb absorption line at $\lambda$ex=415 nm. No significant photobleaching of the cells was observed.

Although the tryptophan and PN peaks were present in all samples, the intensity of the PN and Fp peaks and other features varied greatly among the pellet sample EEM's. FIG. 3 shows an EEM of a sample with the (430,520) peak more pronounced. The Sorer absorption band is also clearly visible, while the (250,400) peak is absent completely. For the sample EEM in FIG. 4, the peak at (250,400) is even more intense than the (280,330) tryptophan peak.

Table 1 lists these spectral features, and the average and standard deviation for each. All features showed considerable variation among samples, with the magnitude of the standard deviation exceeding the mean in most cases. The (280,330) peak stability can be attributed to the fact that the spectra were normalized to the nearby (270,330) value. The EEM value with the least percent variance was at (300,360), between the tryptophan and PN peaks.

TABLE 1

SPECTRAL FEATURES OF CELL PELLET EEM's*

| feature | all samples | | nor. sample | | abn. samples | | nor v abn |
|---|---|---|---|---|---|---|---|
| ($\lambda$em,$\lambda$ex) | $\mu$ | $\sigma$ | $\mu$ | $\sigma$ | $\mu$ | $\sigma$ | p |
| (280,330) | 1.18 | 0.16 | 1.16 | 0.16 | 1.19 | 0.17 | 0.56 |
| (250,400) | 0.29 | 0.61 | 0.33 | 0.62 | 0.28 | 0.62 | 0.78 |
| (280,450) | 0.08 | 0.09 | 0.08 | 0.09 | 0.08 | 0.09 | 0.93 |
| (370,450) | 0.23 | 0.31 | 0.21 | 0.29 | 0.24 | 0.33 | 0.75 |
| (430,520) | 0.11 | 0.13 | 0.09 | 0.10 | 0.12 | 0.15 | 0.45 |
| (280,450) / (370,450) | 0.36 | 0.21 | 0.40 | 0.32 | 0.34 | 0.28 | 0.08 |
| (300,360) | 0.44 | 0.13 | 0.39 | 0.11 | 0.46 | 0.13 | 0.04 |

* - all values normalized to intensity at (270,330)

Table 1 also compares population statistics for the normal and abnormal sample groups. For each feature, the variance within each group exceeded the difference between the two groups, as reflected in the high p-values. The lowest p-scores for all values or ratios of values in the EEMs are at the ratio of (280,450)/(370,450) and at (300,360).

In order to test the hypothesis that a combination of several variables may identify significant differences between normal and abnormal cells, principal component analysis (PCA) was used to generate a reduced set of variables which are linear combinations of the EEM values. From each EEM, 25 principal components (PC's) accounting for 99.99% of the variance between all samples were calculated. None of the PC's had a higher statistical significance than any of the features in Table 1. Table 2 provides this comparison.

TABLE 2

| pc # | % VAR | mean-nor | mean-ab | sidev-nor | sidev-ab | p-score |
|---|---|---|---|---|---|---|
| *18 | 0.0193 | 0.0207 | 0.0107 | 0.0507 | 0.0324 | 0.041305 |
| * 5 | 1.4136 | −0.1318 | 0.0682 | 0.3042 | 0.3685 | 0.063457 |
| * 3 | 4.3008 | −0.2137 | 0.1105 | 0.5753 | 0.6279 | 0.096108 |
| 22 | 0.0047 | 0.0050 | −0.0026 | 0.0144 | 0.0229 | 0.187096 |
| *16 | 0.0364 | 0.0150 | −0.0077 | 0.0491 | 0.0605 | 0.188685 |
| 23 | 0.0036 | 0.0042 | −0.0022 | 0.0169 | 0.0184 | 0.25996 |
| *10 | 0.1573 | 0.0284 | −0.0147 | 0.1183 | 0.1191 | 0.263165 |
| 19 | 0.0106 | 0.0074 | −0.0038 | 0.0338 | 0.0292 | 0.28409 |
| 13 | 0.0627 | 0.0146 | −0.0076 | 0.0651 | 0.0801 | 0.329235 |
| 25 | 0.0023 | 0.0032 | −0.0016 | 0.0181 | 0.0120 | 0.363534 |
| 14 | 0.0463 | 0.0122 | −0.0063 | 0.0663 | 0.0641 | 0.382071 |
| 12 | 0.0801 | −0.0139 | 0.0072 | 0.0946 | 0.0806 | 0.469852 |
| 15 | 0.0442 | 0.0084 | −0.0043 | 0.0694 | 0.0605 | 0.553599 |
| 8 | 0.3687 | −0.0211 | 0.0109 | 0.1569 | 0.1962 | 0.561494 |
| 7 | 0.5198 | 0.0243 | −0.0126 | 0.2173 | 0.2192 | 0.599062 |
| 1 | 66.9477 | −0.2033 | 0.1052 | 2.1941 | 2.6173 | 0.682091 |
| 21 | 0.0062 | 0.0019 | −0.0010 | 0.0226 | 0.0246 | 0.695786 |
| 17 | 0.0224 | 0.0039 | −0.0020 | 0.0534 | 0.0408 | 0.707169 |
| 9 | 0.2596 | −0.0104 | 0.0054 | 0.1533 | 0.1555 | 0.75051 |
| 20 | 0.0079 | −0.0013 | 0.0007 | 0.0233 | 0.0288 | 0.800828 |
| 24 | 0.0031 | −0.0006 | 0.0003 | 0.0196 | 0.0156 | 0.876723 |
| 2 | 22.881 | −0.0348 | 0.0180 | 1.4811 | 1.4414 | 0.910808 |
| 4 | 1.9629 | 0.0080 | −0.0042 | 0.4774 | 0.3980 | 0.933139 |
| 6 | 0.7267 | 0.0039 | −0.0020 | 0.2047 | 0.2826 | 0.936508 |
| 11 | 0.112 | 0.0005 | −0.0003 | 0.1313 | 0.0832 | 0.983305 |

* used in Dx algorithm total % VAR used = 5.927%

Figure 5:
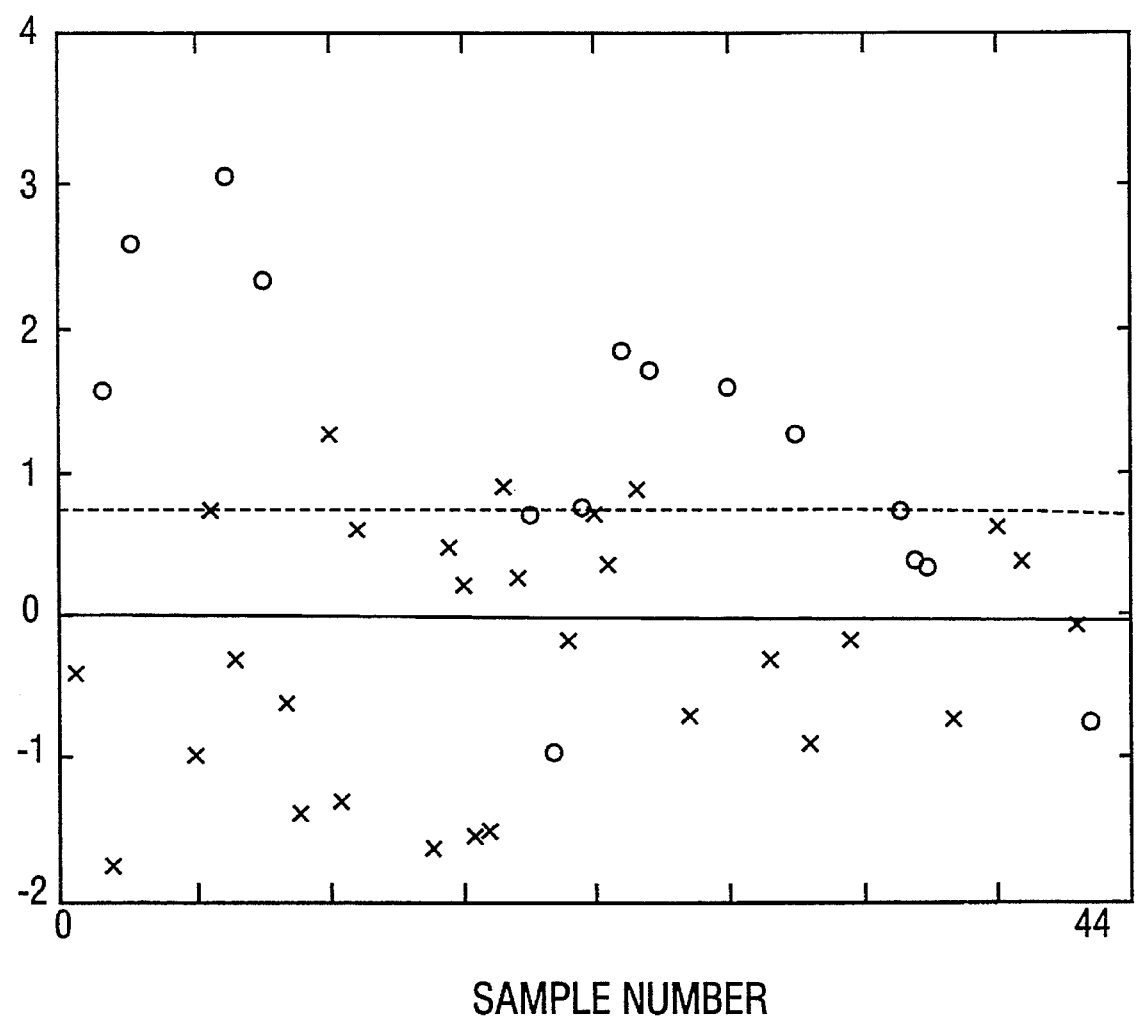
FIG. 5 is a scattergram of cell pellet classification based on principal component analysis of EEM's. (x) indicates samples deemed abnormal by Pap smear reading and (o) indicates samples deemed normal by Pap smear reading.
Figure 6:
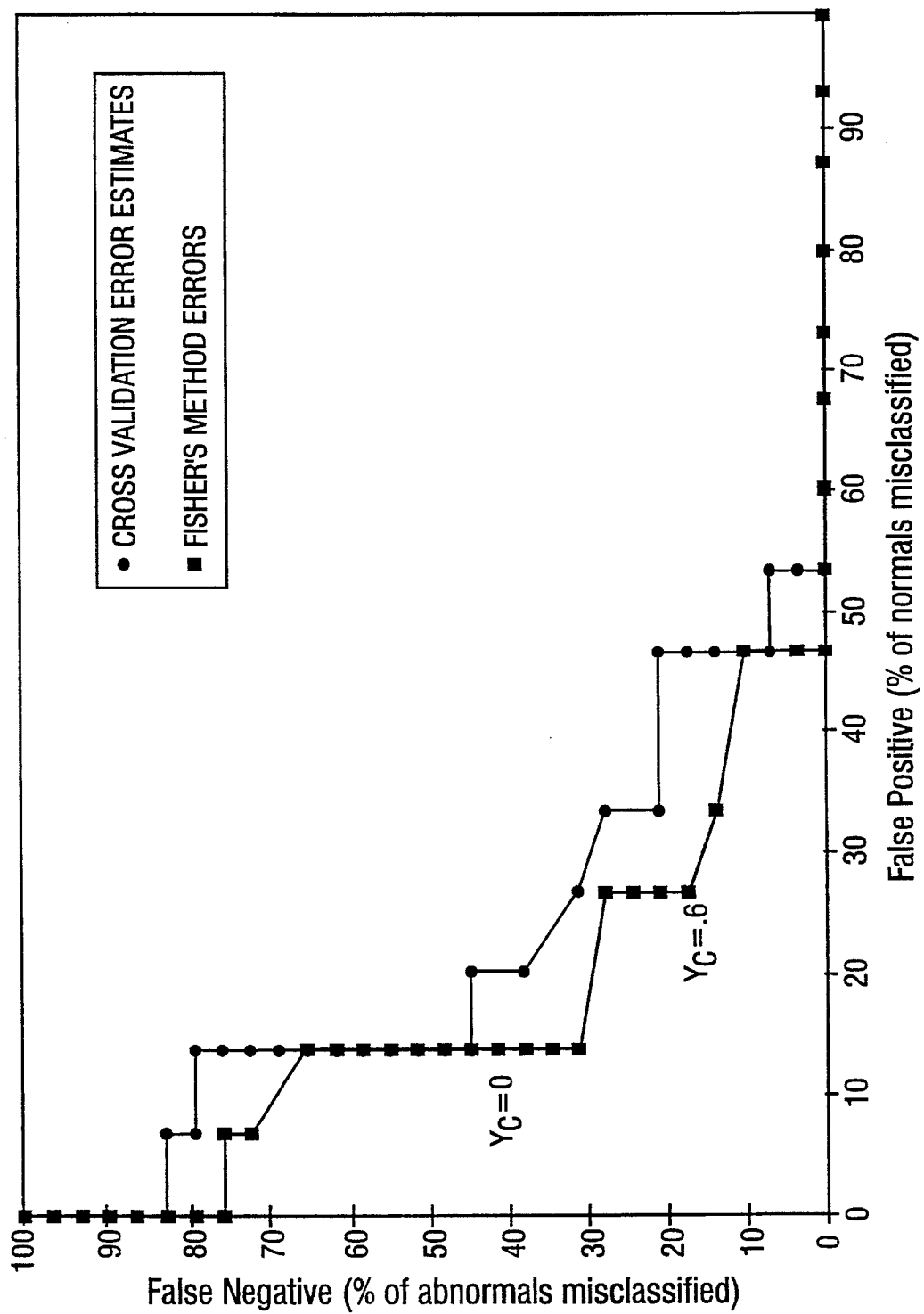
FIG. 6 is a graph showing classification errors for Fisher's discriminant analysis.

A discriminant function was found using Fisher's discriminant analysis (FDA), assuming equal prior probabilities and variable cost of misclassification. This function used 5 of the PCs above which together account for 5.93% of the sample-to-sample variance (3,5,10,16,18). The discriminant score calculated for each sample is plotted in FIG. 5, where samples above $Y_c$ are classified as normal, samples below $Y_c$ abnormals. The Pap smear diagnosis is shown as well (o - normals, x - abnormals). The false positive rate (FP) is 2/15=13.4%, while the false negative rate (FN) is 12/29= 41.4%, where the $Y_c$ is 0 (solid line). Another choice is $Y_c$ is 0.6, where the FN is 4/29=13.8% and the FP is 5/15= 33.3% (broken line). A plot of the FN versus FP, obtained by varying $Y_c$ in FIG. 5, is shown in FIG. 6, with the diagonal line representing random classification. The expected performance of the discriminant function on additional samples was estimated using cross validation, with the results shown in FIG. 6.

E. ThinPrep vs Pellet Autofluorescence

Figure 7:
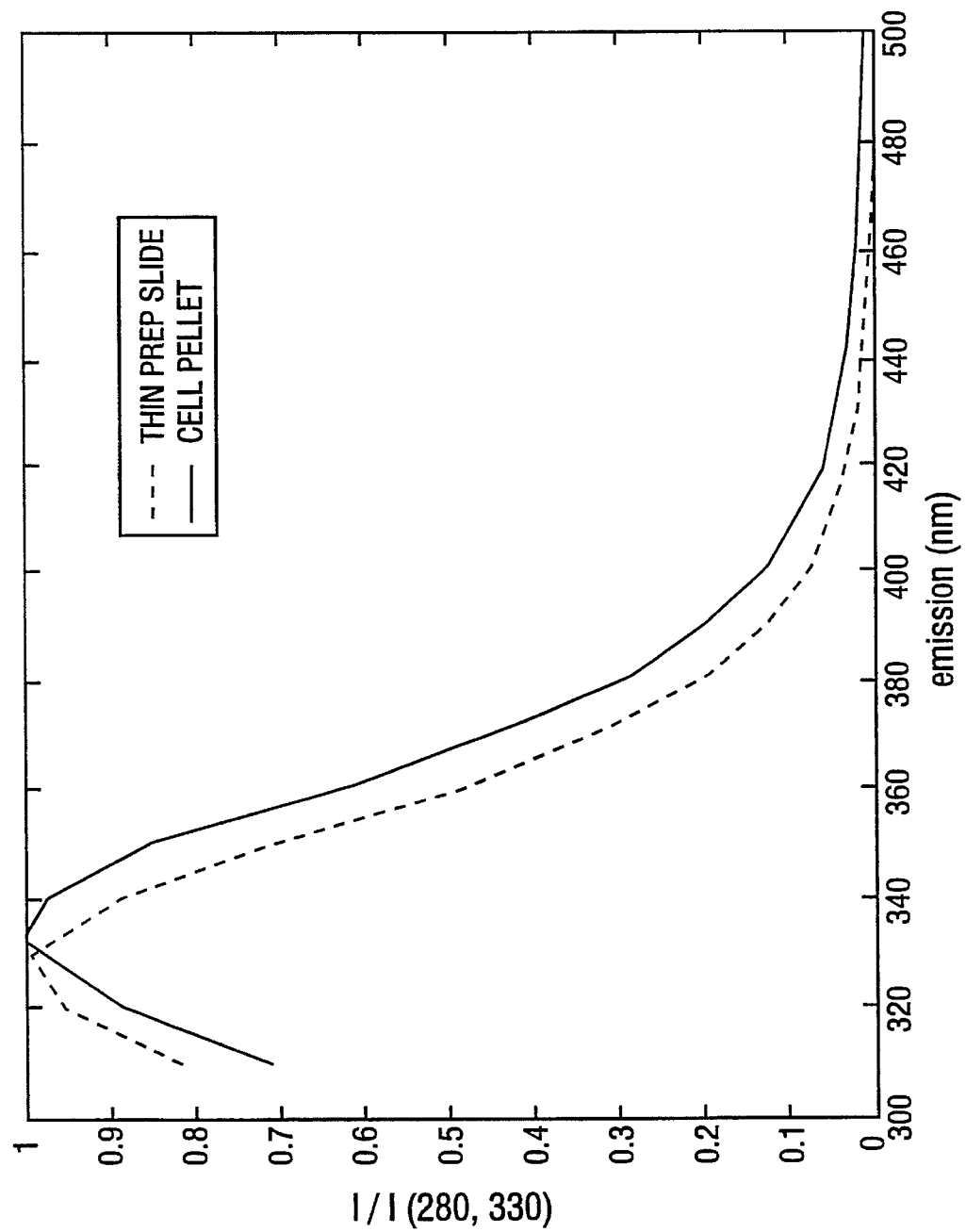
FIG. 7 is a graph of typical ThinPrep versus Pellet Spectra for 280 nm excitation wavelength.
Figure 8:
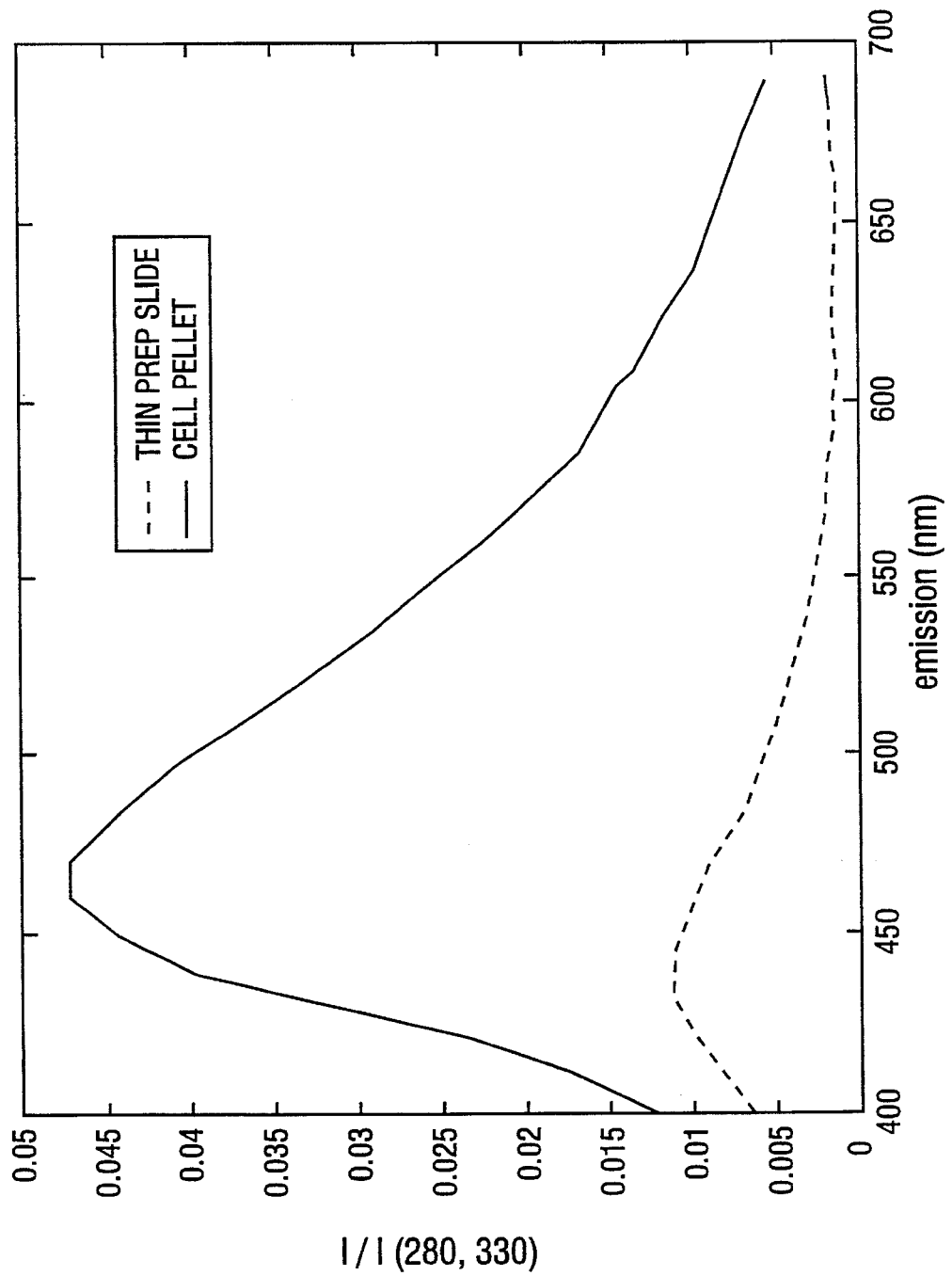
FIG. 8 is a graph of typical ThinPrep versus Pellet Spectra for 370 nm excitation wavelength.

FIG. 7 compares ThinPrep and pellet emission spectra from a typical sample for 280 nm excitation. For all samples, the spectra are similar in shape, except that the ThinPrep spectra are blue shifted by an average of 10 nm. In FIG. 8, the spectra at 370 nm excitation are compared for a typical case. Again, the ThinPrep spectrum is blue-shifted with respect to the pellet spectrum. In addition, the intensity at the ThinPrep PN peak around (370,450) is 5- to 10-times lower than the corresponding pellet spectra. The variance between samples is reduced for the ThinPrep spectra, having a lower standard deviation as a percentage of the mean, 58%, compared to 82% for the pellet data. The excitation spectra of the ThinPrep slides recorded at 440 nm emission showed considerable variance below 350 nm excitation due to the strong UV emission of the glass slides. Above 350 nm excitation, the spectra differed from the pellet spectra in the degree of variance between samples and in the intensity, as described above for the (370,450) peak.

APPENDIX I: SPECIFICITY AND SENSITIVITY

Summarized from: Albert A., Harris E. K.: *Multivariate Interpretation of Clinical Laboratory Data*, Marcel Dekker Inc., New York, pp. 75–82, (1987), the disclosure of which is expressly incorporated herein by reference.

Figure 9:
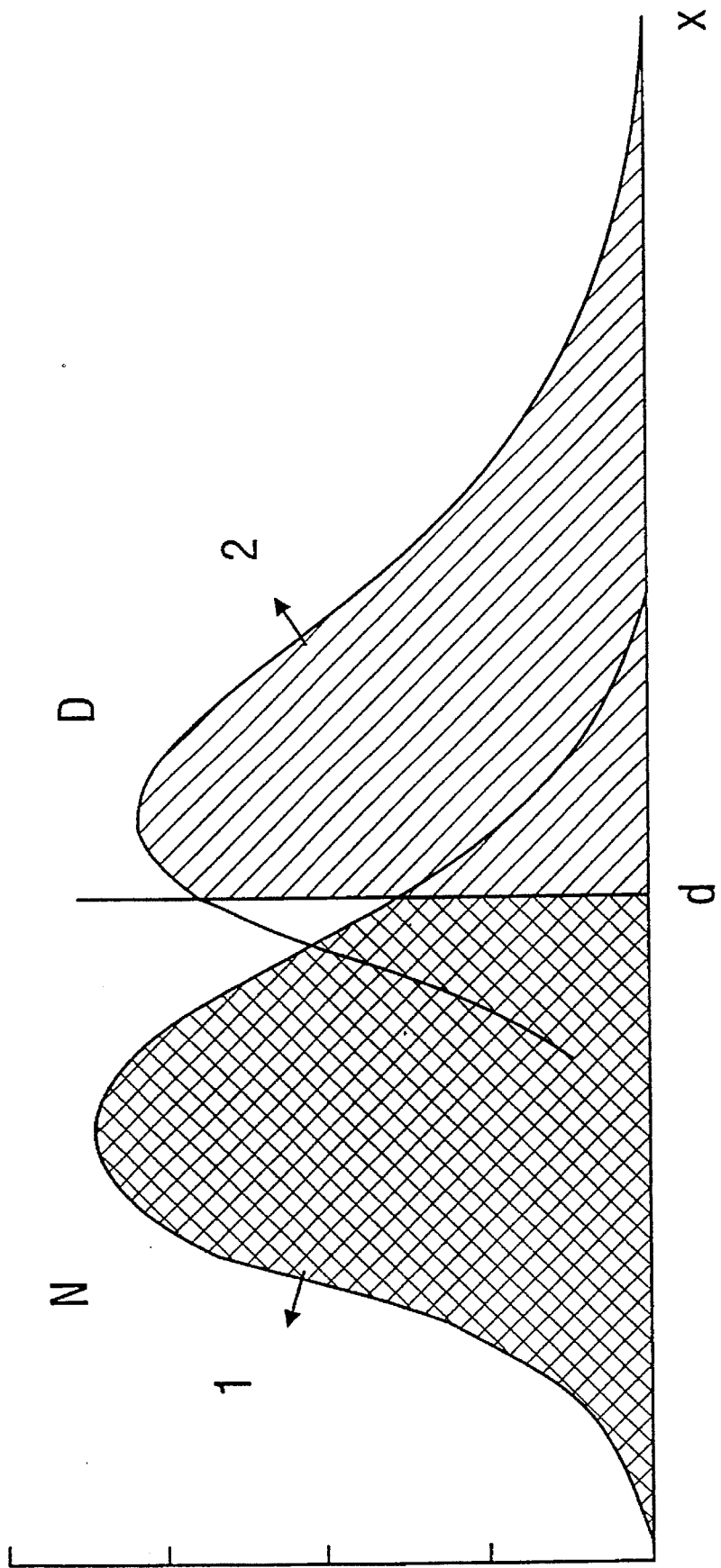
FIG. 9 is a graph of a hypothetical distribution of test values for hypothetical samples.

Assuming a group of T samples which can be categorized as normal (N samples) or diseased (D samples). A diagnostic test, designed to determine whether the sample is normal or diseased, is applied to each sample. The results of the tests is the continuous variable x, which is then used to determine the sample type. FIG. 9 illustrates a hypothetical distribution of test values for each sample type. A diagnostic method based on this test can easily be defined by choosing a cutoff point, d, such that a sample with an observed value x<d is diagnosed as normal and a sample with an observed value x≧d is diagnosed as abnormal.

Several quantitative measures have been defined to 'evaluate' the performance of this type of method. The first type evaluates the test itself (i.e., measures the ability of the test to separate the two populations, N and D). Sensitivity and specificity are two such measures. The second type is designed to aid in the interpretation of a particular test result (i.e. deciding whether the individual test measurement has come from a normal or diseased sample). Positive and negative predictive value are two measures of this type.

To define these measures, some terminology and notation must be introduced. Referring to Table 3, a sample to be tested can be either normal or diseased; the result of the test for each type of sample can be either negative or positive. True negatives represent those normal with a positive test result. In these cases, the diagnosis based on the rest result is correct. False positives are those normal samples which have a positive test result and false negatives are those diseased samples which have a negative test result. In these cases, the diagnosis based on the test result is incorrect.

TABLE 3

|  | Normal | Diseased | Total Samples |
|---|---|---|---|
| Test Negative (x < d) | True Negatives (TN) | False Negatives (FN) | Negatives (Neg) |
| Test Positive (x ≧ d) | False Positives (FP) | True Positives (TP) | Positives (Pos) |
| Total Samples | N | D | T |

With this terminology, Table 4 contains a definition of sensitivity and specificity, the two measures which assess the performance of the diagnostic method. Specificity is the proportion of normal samples with a negative test result (proportion of normal samples diagnosed correctly). Sensitivity is the proportion of diseased samples with a positive test result (Proportion of diseased samples correctly diagnosed). FIG. 9 also contains a graphical representation of specificity and sensitivity. Specificity represents the area under the normal sample distribution curve to the left of the cut off point while sensitivity represent the area under the diseased sample distribution curve to the right of the cut off point.

TABLE 4

| Test Measure | Meaning | Calculation |
|---|---|---|
| Specificity | Proportion of normal samples with negative test result | Sp = TN/N |
| Sensitivity | Proportion of diseased samples with positive test result | Se = TP/D |

While sensitivity and specificity characterize the performance of a particular method, another set of statistics is required to interpret the laboratory test result for a given specimen. The positive and negative predictive value quantify the meaning of an individual test result (Table 5). The positive predictive value is the probability that if the test result is positive, the sample is diseased. The negative predictive value is the probability that if the test result is negative, the sample is normal. Positive and negative predictive value are calculated from Baye's rule as outlined in Albert and Harris. Table 5 contains two equivalent formulas for calculation positive and negative predictive value.

TABLE 5

| Measure | Meaning | Calculation 1 | Calculation 2 |
|---|---|---|---|
| Positive Predictive Value | The probability that, if the test is positive, the sample is diseased | $PV_+ = TP/Pos$ | $PV_+ = DSe/(DSe + N(1-Sp))$ |
| Negative Predictive Value | The probability that, if the test is negative, the sample is normal | $PV_- = TN/Neg$ | $PV_- = NSp/(NSp + D(1-Se))$ |

| ex(nm) | em(nm) | evec3 | evec5 | evec10 | evec16 | evec18 |
|---|---|---|---|---|---|---|
| 250 | 280 | 0.155 | 0.353 | −0.031 | −0.058 | −0.055 |
| 250 | 290 | 0.058 | 0.097 | −0.020 | 0.077 | 0.109 |
| 250 | 300 | 0.024 | 0.055 | −0.033 | 0.035 | 0.096 |
| 250 | 310 | 0.028 | 0.106 | −0.023 | 0.064 | 0.186 |
| 250 | 320 | 0.037 | 0.153 | 0.000 | 0.119 | 0.168 |
| 250 | 330 | 0.016 | 0.188 | −0.001 | 0.052 | 0.034 |
| 250 | 340 | −0.004 | 0.197 | −0.012 | −0.003 | −0.064 |
| 250 | 350 | −0.014 | 0.187 | −0.046 | −0.030 | −0.140 |
| 250 | 360 | −0.015 | 0.132 | −0.051 | −0.029 | −0.134 |
| 250 | 370 | −0.011 | 0.060 | −0.040 | −0.010 | −0.110 |
| 250 | 380 | −0.004 | −0.017 | −0.013 | 0.012 | −0.039 |
| 250 | 390 | −0.003 | −0.069 | 0.019 | 0.021 | −0.010 |
| 250 | 400 | −0.005 | −0.088 | 0.049 | −0.001 | 0.010 |
| 250 | 410 | −0.010 | −0.082 | 0.051 | −0.009 | 0.006 |
| 250 | 420 | −0.012 | −0.061 | 0.046 | −0.008 | 0.061 |
| 250 | 430 | −0.013 | −0.047 | 0.044 | −0.006 | 0.059 |
| 250 | 440 | −0.013 | −0.031 | 0.038 | 0.003 | 0.063 |
| 250 | 450 | −0.013 | −0.022 | 0.041 | −0.001 | 0.060 |
| 250 | 460 | −0.010 | −0.014 | 0.034 | 0.006 | 0.054 |
| 260 | 290 | −0.013 | 0.017 | −0.063 | −0.046 | −0.101 |
| 260 | 300 | −0.030 | −0.026 | −0.102 | −0.134 | −0.044 |
| 260 | 310 | −0.009 | 0.007 | −0.093 | −0.019 | 0.085 |
| 260 | 320 | −0.003 | 0.035 | −0.078 | 0.054 | 0.160 |
| 260 | 330 | −0.029 | 0.060 | −0.091 | 0.036 | 0.052 |
| 260 | 340 | −0.045 | 0.085 | −0.121 | −0.009 | −0.008 |
| 260 | 350 | −0.046 | 0.087 | −0.143 | −0.031 | −0.088 |
| 260 | 360 | −0.037 | 0.066 | −0.136 | −0.004 | −0.119 |
| 260 | 370 | −0.029 | 0.042 | −0.115 | −0.005 | −0.094 |
| 260 | 380 | −0.023 | 0.015 | −0.077 | −0.006 | −0.088 |
| 260 | 390 | −0.021 | −0.007 | −0.039 | −0.011 | −0.062 |
| 260 | 400 | −0.021 | −0.021 | −0.010 | −0.022 | −0.048 |
| 260 | 410 | −0.023 | −0.025 | 0.010 | −0.030 | −0.039 |
| 260 | 420 | −0.023 | −0.023 | 0.022 | −0.031 | −0.009 |
| 260 | 430 | −0.022 | −0.023 | 0.031 | −0.027 | −0.024 |
| 260 | 440 | −0.021 | −0.020 | 0.037 | −0.029 | −0.026 |
| 260 | 450 | −0.019 | −0.018 | 0.046 | −0.028 | −0.026 |
| 260 | 460 | −0.016 | −0.015 | 0.044 | −0.024 | −0.032 |
| 260 | 470 | −0.014 | −0.014 | 0.044 | −0.023 | −0.027 |
| 260 | 480 | −0.012 | −0.011 | 0.039 | −0.020 | −0.020 |
| 270 | 300 | −0.032 | −0.105 | −0.059 | 0.017 | −0.173 |
| 270 | 310 | 0.008 | −0.068 | −0.036 | −0.005 | −0.040 |
| 270 | 320 | 0.026 | −0.035 | −0.014 | 0.006 | 0.028 |
| 270 | 330 | 0.000 | 0.000 | 0.000 | 0.000 | 0.000 |
| 270 | 340 | −0.020 | 0.038 | −0.025 | 0.011 | 0.002 |
| 270 | 350 | −0.026 | 0.046 | −0.058 | 0.073 | −0.024 |
| 270 | 360 | −0.021 | 0.035 | −0.062 | 0.124 | −0.039 |
| 270 | 370 | −0.017 | 0.017 | −0.058 | 0.140 | −0.048 |
| 270 | 380 | −0.016 | 0.004 | −0.036 | 0.115 | −0.042 |
| 270 | 390 | −0.020 | −0.005 | −0.009 | 0.086 | −0.035 |
| 270 | 400 | −0.024 | −0.012 | 0.011 | 0.062 | −0.038 |
| 270 | 410 | −0.030 | −0.016 | 0.027 | 0.046 | −0.042 |
| 270 | 420 | −0.031 | −0.014 | 0.040 | 0.035 | −0.011 |
| 270 | 430 | −0.031 | −0.016 | 0.051 | 0.035 | −0.038 |
| 270 | 440 | −0.030 | −0.015 | 0.059 | 0.028 | −0.040 |
| 270 | 450 | −0.027 | −0.015 | 0.066 | 0.022 | −0.042 |
| 270 | 460 | −0.023 | −0.015 | 0.064 | 0.018 | −0.048 |
| 270 | 470 | −0.020 | −0.013 | 0.060 | 0.013 | −0.048 |
| 270 | 480 | −0.017 | −0.012 | 0.055 | 0.011 | −0.037 |
| 270 | 490 | −0.015 | −0.012 | 0.048 | 0.012 | −0.024 |
| 270 | 500 | −0.013 | −0.011 | 0.042 | 0.011 | −0.008 |
| 280 | 310 | 0.168 | −0.238 | −0.057 | 0.027 | −0.099 |
| 280 | 320 | 0.225 | −0.213 | −0.037 | 0.000 | −0.067 |
| 280 | 330 | 0.223 | −0.196 | −0.046 | 0.007 | −0.052 |
| 280 | 340 | 0.200 | −0.159 | −0.089 | 0.063 | −0.006 |
| 280 | 350 | 0.161 | −0.124 | −0.136 | 0.113 | 0.008 |
| 280 | 360 | 0.118 | −0.089 | −0.137 | 0.126 | 0.033 |
| 280 | 370 | 0.079 | −0.065 | −0.122 | 0.104 | 0.028 |
| 280 | 380 | 0.045 | −0.048 | −0.091 | 0.073 | 0.024 |
| 280 | 390 | 0.020 | −0.040 | −0.049 | 0.042 | 0.014 |
| 280 | 400 | −0.001 | −0.035 | −0.022 | 0.024 | 0.006 |
| 280 | 410 | −0.014 | −0.030 | 0.001 | 0.009 | 0.011 |
| 280 | 420 | −0.020 | −0.023 | 0.018 | −0.004 | 0.031 |
| 280 | 430 | −0.022 | −0.022 | 0.031 | 0.001 | 0.000 |
| 280 | 440 | −0.023 | −0.021 | 0.041 | −0.002 | −0.009 |
| 280 | 450 | −0.021 | −0.020 | 0.048 | 0.000 | −0.012 |
| 280 | 460 | −0.018 | −0.019 | 0.051 | 0.001 | −0.024 |
| 280 | 470 | −0.016 | −0.018 | 0.049 | 0.000 | −0.031 |
| 280 | 480 | −0.014 | −0.017 | 0.046 | 0.001 | −0.032 |
| 280 | 490 | −0.012 | −0.016 | 0.042 | 0.002 | −0.018 |
| 280 | 500 | −0.010 | −0.014 | 0.037 | 0.006 | −0.011 |
| 280 | 510 | −0.009 | −0.013 | 0.032 | 0.006 | −0.005 |
| 280 | 520 | −0.008 | −0.012 | 0.029 | 0.003 | −0.005 |
| 290 | 320 | 0.348 | −0.068 | 0.019 | −0.279 | 0.024 |
| 290 | 330 | 0.363 | −0.066 | 0.015 | −0.231 | −0.020 |
| 290 | 340 | 0.335 | −0.053 | −0.048 | −0.104 | 0.010 |
| 290 | 350 | 0.278 | −0.040 | −0.113 | −0.007 | 0.012 |
| 290 | 360 | 0.204 | −0.029 | −0.137 | 0.057 | 0.023 |
| 290 | 370 | 0.140 | −0.027 | −0.129 | 0.065 | 0.017 |
| 290 | 380 | 0.083 | −0.028 | −0.097 | 0.041 | 0.002 |
| 290 | 390 | 0.044 | −0.030 | −0.064 | 0.015 | 0.000 |
| 290 | 400 | 0.016 | −0.032 | −0.034 | −0.007 | 0.002 |
| 290 | 410 | −0.002 | −0.003 | −0.015 | −0.020 | 0.007 |
| 290 | 420 | −0.010 | −0.024 | 0.002 | −0.033 | 0.030 |
| 290 | 430 | −0.012 | −0.024 | 0.014 | 0.028 | 0.006 |
| 290 | 440 | −0.013 | −0.023 | 0.023 | −0.027 | −0.005 |
| 290 | 450 | −0.012 | −0.023 | 0.033 | −0.021 | −0.012 |
| 290 | 460 | −0.010 | −0.023 | 0.036 | −0.016 | −0.026 |
| 290 | 470 | −0.009 | −0.022 | 0.036 | −0.013 | −0.027 |
| 290 | 480 | −0.007 | −0.020 | 0.036 | −0.011 | −0.025 |
| 290 | 490 | −0.006 | −0.019 | 0.034 | −0.007 | −0.024 |
| 290 | 500 | −0.005 | −0.019 | 0.030 | −0.003 | −0.021 |
| 290 | 510 | −0.004 | −0.018 | 0.028 | −0.001 | −0.018 |
| 290 | 520 | −0.004 | −0.017 | 0.026 | −0.001 | −0.012 |
| 290 | 530 | −0.003 | −0.016 | 0.024 | −0.004 | −0.011 |
| 290 | 540 | −0.003 | −0.015 | 0.022 | −0.003 | −0.007 |
| 300 | 330 | 0.230 | 0.211 | 0.331 | −0.028 | 0.004 |
| 300 | 340 | 0.221 | 0.226 | 0.276 | 0.058 | −0.019 |
| 300 | 350 | 0.184 | 0.212 | 0.168 | 0.105 | −0.024 |
| 300 | 360 | 0.136 | 0.171 | 0.081 | 0.104 | −0.021 |
| 300 | 370 | 0.093 | 0.125 | 0.021 | 0.075 | −0.019 |
| 300 | 380 | 0.054 | 0.077 | −0.006 | 0.030 | −0.008 |
| 300 | 390 | 0.027 | 0.041 | −0.015 | −0.007 | −0.005 |
| 300 | 400 | 0.007 | 0.012 | −0.017 | −0.035 | −0.006 |
| 300 | 410 | −0.005 | −0.002 | −0.017 | −0.049 | −0.008 |
| 300 | 420 | −0.010 | −0.007 | −0.010 | −0.057 | 0.015 |
| 300 | 430 | −0.010 | −0.012 | −0.005 | −0.048 | −0.010 |
| 300 | 440 | −0.009 | −0.013 | 0.001 | −0.045 | −0.013 |
| 300 | 450 | −0.007 | −0.015 | 0.010 | −0.037 | −0.015 |
| 300 | 460 | −0.005 | −0.016 | 0.014 | −0.028 | −0.026 |
| 300 | 470 | −0.003 | −0.016 | 0.017 | −0.024 | −0.031 |
| 300 | 480 | −0.002 | −0.016 | 0.019 | −0.019 | −0.028 |
| 300 | 490 | 0.000 | −0.016 | 0.019 | −0.013 | −0.026 |
| 300 | 500 | 0.000 | −0.016 | 0.019 | −0.008 | −0.021 |
| 300 | 510 | 0.001 | −0.015 | 0.018 | −0.006 | −0.024 |
| 300 | 520 | 0.001 | −0.015 | 0.018 | −0.006 | −0.018 |

| ex(nm) | em(nm) | evec3 | evec5 | evec10 | evec16 | evec18 |
|---|---|---|---|---|---|---|
| 300 | 530 | 0.001 | −0.014 | 0.018 | −0.007 | −0.018 |
| 300 | 540 | 0.001 | −0.013 | 0.016 | −0.007 | −0.015 |
| 300 | 550 | 0.001 | −0.012 | 0.016 | −0.007 | −0.015 |
| 300 | 560 | 0.001 | −0.010 | 0.013 | −0.007 | −0.015 |
| 310 | 340 | 0.004 | 0.052 | 0.029 | −0.010 | −0.021 |
| 310 | 350 | −0.002 | 0.058 | −0.003 | −0.035 | −0.030 |
| 310 | 360 | −0.006 | 0.051 | −0.026 | −0.055 | −0.010 |
| 310 | 370 | −0.009 | 0.039 | −0.042 | −0.073 | −0.003 |
| 310 | 380 | −0.012 | 0.025 | −0.047 | −0.084 | 0.020 |
| 310 | 390 | −0.013 | 0.012 | −0.043 | −0.088 | 0.025 |
| 310 | 400 | −0.015 | 0.000 | −0.042 | −0.080 | 0.008 |
| 310 | 410 | −0.017 | −0.007 | −0.039 | −0.077 | −0.002 |
| 310 | 420 | −0.017 | −0.007 | −0.029 | −0.073 | 0.017 |
| 310 | 430 | −0.014 | −0.012 | −0.023 | −0.054 | −0.019 |
| 310 | 440 | −0.012 | −0.011 | −0.016 | −0.047 | −0.025 |
| 310 | 450 | −0.008 | −0.012 | −0.006 | −0.036 | 0.024 |
| 310 | 460 | −0.004 | −0.013 | 0.001 | −0.024 | −0.037 |
| 310 | 470 | −0.002 | −0.012 | 0.004 | −0.016 | −0.038 |
| 310 | 480 | 0.000 | −0.012 | 0.007 | −0.009 | −0.037 |
| 310 | 490 | 0.001 | −0.012 | 0.009 | −0.003 | −0.035 |
| 310 | 500 | 0.002 | −0.012 | 0.009 | 0.002 | −0.032 |
| 310 | 510 | 0.003 | −0.011 | 0.011 | 0.004 | −0.027 |
| 310 | 520 | 0.003 | −0.011 | 0.011 | 0.004 | −0.024 |
| 310 | 530 | 0.003 | −0.011 | 0.013 | 0.003 | −0.023 |
| 310 | 540 | 0.003 | −0.010 | 0.012 | 0.002 | −0.022 |
| 310 | 550 | 0.003 | −0.009 | 0.011 | 0.001 | −0.018 |
| 310 | 560 | 0.003 | −0.008 | 0.009 | 0.002 | −0.016 |
| 310 | 570 | 0.002 | −0.007 | 0.008 | 0.001 | −0.016 |
| 310 | 580 | 0.002 | −0.006 | 0.006 | 0.000 | −0.014 |
| 320 | 350 | −0.019 | 0.017 | −0.041 | −0.101 | −0.022 |
| 320 | 360 | −0.020 | 0.015 | −0.054 | −0.129 | 0.000 |
| 320 | 370 | −0.020 | 0.013 | −0.060 | −0.141 | 0.011 |
| 320 | 380 | −0.020 | 0.007 | −0.059 | −0.138 | 0.040 |
| 320 | 390 | −0.019 | 0.000 | −0.053 | −0.125 | 0.045 |
| 320 | 400 | −0.018 | −0.008 | −0.047 | −0.101 | 0.023 |
| 320 | 410 | −0.019 | −0.014 | −0.045 | −0.084 | 0.004 |
| 320 | 420 | −0.018 | −0.013 | −0.034 | −0.071 | 0.028 |
| 320 | 430 | −0.013 | −0.017 | −0.029 | −0.044 | −0.018 |
| 320 | 440 | −0.010 | −0.016 | −0.022 | −0.031 | −0.025 |
| 320 | 450 | −0.006 | −0.016 | −0.010 | −0.018 | −0.025 |
| 320 | 460 | −0.002 | −0.017 | −0.005 | −0.005 | −0.040 |
| 320 | 470 | 0.000 | −0.015 | −0.001 | 0.001 | −0.041 |
| 320 | 480 | 0.002 | −0.013 | 0.003 | 0.005 | −0.036 |
| 320 | 490 | 0.003 | −0.013 | 0.005 | 0.013 | −0.035 |
| 320 | 500 | 0.004 | −0.012 | 0.005 | 0.016 | −0.030 |
| 320 | 510 | 0.004 | −0.012 | 0.007 | 0.017 | −0.026 |
| 320 | 520 | 0.004 | −0.011 | 0.008 | 0.016 | −0.024 |
| 320 | 530 | 0.004 | −0.010 | 0.009 | 0.014 | −0.021 |
| 320 | 540 | 0.004 | −0.009 | 0.009 | 0.011 | −0.023 |
| 320 | 550 | 0.004 | −0.008 | 0.008 | 0.010 | −0.020 |
| 320 | 560 | 0.003 | −0.008 | 0.007 | 0.008 | −0.018 |
| 320 | 570 | 0.003 | −0.007 | 0.006 | 0.007 | −0.016 |
| 320 | 580 | 0.003 | −0.006 | 0.005 | 0.005 | −0.014 |
| 320 | 590 | 0.002 | −0.005 | 0.004 | 0.004 | −0.015 |
| 320 | 600 | 0.002 | −0.004 | 0.003 | 0.004 | −0.012 |
| 330 | 360 | −0.015 | 0.013 | −0.046 | −0.096 | 0.010 |
| 330 | 370 | −0.016 | 0.011 | −0.053 | −0.109 | 0.031 |
| 330 | 380 | −0.016 | 0.007 | −0.053 | −0.107 | 0.071 |
| 330 | 390 | −0.016 | −0.001 | −0.046 | −0.099 | 0.076 |
| 330 | 400 | −0.016 | −0.010 | −0.046 | −0.075 | 0.036 |
| 330 | 410 | −0.018 | −0.017 | −0.047 | −0.058 | 0.000 |
| 330 | 420 | −0.017 | −0.016 | −0.033 | −0.049 | 0.033 |
| 330 | 430 | −0.013 | −0.022 | −0.029 | −0.017 | −0.028 |
| 330 | 440 | −0.009 | −0.021 | −0.022 | −0.006 | −0.028 |
| 330 | 450 | −0.005 | −0.020 | −0.008 | 0.004 | −0.022 |
| 330 | 460 | −0.001 | −0.021 | −0.003 | 0.017 | −0.042 |
| 330 | 470 | 0.002 | −0.018 | 0.001 | 0.020 | −0.038 |
| 330 | 480 | 0.003 | −0.016 | 0.004 | 0.023 | −0.028 |
| 330 | 490 | 0.005 | −0.015 | 0.005 | 0.029 | −0.025 |
| 330 | 500 | 0.006 | −0.014 | 0.006 | 0.031 | −0.024 |
| 330 | 510 | 0.006 | −0.013 | 0.006 | 0.030 | −0.020 |
| 330 | 520 | 0.006 | −0.012 | 0.007 | 0.028 | −0.013 |
| 330 | 530 | 0.005 | −0.011 | 0.009 | 0.023 | −0.014 |
| 330 | 540 | 0.005 | −0.010 | 0.009 | 0.020 | −0.013 |
| 330 | 550 | 0.004 | −0.009 | 0.008 | 0.016 | −0.012 |
| 330 | 560 | 0.004 | −0.007 | 0.007 | 0.013 | −0.012 |
| 330 | 570 | 0.004 | −0.006 | 0.005 | 0.011 | −0.009 |
| 330 | 580 | 0.003 | −0.006 | 0.005 | 0.008 | −0.013 |
| 330 | 590 | 0.003 | −0.004 | 0.003 | 0.006 | −0.011 |
| 330 | 600 | 0.003 | −0.003 | 0.002 | 0.006 | −0.011 |
| 330 | 610 | 0.002 | −0.003 | 0.002 | 0.005 | −0.010 |
| 330 | 620 | 0.002 | −0.002 | 0.001 | 0.005 | −0.009 |
| 340 | 370 | −0.005 | 0.005 | −0.032 | −0.029 | 0.062 |
| 340 | 380 | −0.007 | 0.004 | −0.035 | −0.030 | 0.114 |
| 340 | 390 | −0.009 | −0.001 | −0.029 | −0.025 | 0.130 |
| 340 | 400 | −0.011 | −0.011 | −0.034 | −0.006 | 0.063 |
| 340 | 410 | −0.015 | −0.018 | −0.042 | 0.005 | 0.001 |
| 340 | 420 | −0.015 | −0.017 | −0.023 | 0.007 | 0.049 |
| 340 | 430 | −0.010 | −0.024 | −0.020 | 0.039 | −0.041 |
| 340 | 440 | −0.006 | −0.023 | −0.012 | 0.042 | −0.036 |
| 340 | 450 | −0.001 | −0.023 | 0.007 | 0.048 | −0.020 |
| 340 | 460 | 0.004 | −0.023 | 0.010 | 0.057 | −0.044 |
| 340 | 470 | 0.006 | −0.020 | 0.012 | 0.051 | −0.039 |
| 340 | 480 | 0.008 | −0.017 | 0.016 | 0.050 | −0.022 |
| 340 | 490 | 0.009 | −0.016 | 0.016 | 0.050 | 0.022 |
| 340 | 500 | 0.009 | −0.014 | 0.014 | 0.048 | −0.013 |
| 340 | 510 | 0.009 | −0.012 | 0.013 | 0.043 | −0.006 |
| 340 | 520 | 0.009 | −0.011 | 0.013 | 0.039 | −0.004 |
| 340 | 530 | 0.008 | −0.010 | 0.013 | 0.032 | −0.002 |
| 340 | 540 | 0.007 | −0.008 | 0.012 | 0.026 | −0.004 |
| 340 | 550 | 0.006 | −0.007 | 0.011 | 0.021 | −0.003 |
| 340 | 560 | 0.005 | −0.006 | 0.010 | 0.016 | −0.006 |
| 340 | 570 | 0.005 | −0.005 | 0.007 | 0.013 | −0.007 |
| 340 | 580 | 0.004 | −0.004 | 0.005 | 0.012 | −0.008 |
| 340 | 590 | 0.004 | −0.003 | 0.004 | 0.009 | −0.007 |
| 340 | 600 | 0.003 | −0.002 | 0.002 | 0.007 | −0.008 |
| 340 | 610 | 0.003 | −0.002 | 0.002 | 0.007 | −0.009 |
| 340 | 620 | 0.003 | −0.001 | 0.002 | 0.006 | −0.010 |
| 340 | 630 | 0.003 | 0.000 | 0.001 | 0.006 | −0.011 |
| 340 | 640 | 0.002 | 0.000 | 0.001 | 0.004 | −0.011 |
| 350 | 380 | −0.004 | 0.003 | −0.025 | 0.007 | 0.119 |
| 350 | 390 | −0.005 | −0.002 | −0.016 | 0.010 | 0.154 |
| 350 | 400 | −0.007 | −0.011 | −0.031 | 0.034 | 0.082 |
| 350 | 410 | −0.013 | −0.019 | −0.047 | 0.038 | 0.016 |
| 350 | 420 | −0.016 | −0.017 | −0.022 | 0.029 | 0.088 |
| 350 | 430 | −0.010 | −0.027 | −0.016 | 0.071 | −0.028 |
| 350 | 440 | −0.006 | −0.025 | −0.007 | 0.065 | −0.005 |
| 350 | 450 | 0.001 | −0.026 | 0.017 | 0.070 | 0.019 |
| 350 | 460 | 0.007 | −0.027 | 0.021 | 0.078 | −0.008 |
| 350 | 470 | 0.009 | −0.023 | 0.020 | 0.068 | 0.003 |
| 350 | 480 | 0.011 | −0.019 | 0.024 | 0.062 | 0.022 |
| 350 | 490 | 0.012 | −0.017 | 0.022 | 0.062 | 0.023 |
| 350 | 500 | 0.012 | −0.015 | 0.018 | 0.059 | 0.028 |
| 350 | 510 | 0.011 | −0.012 | 0.015 | 0.051 | 0.035 |
| 350 | 520 | 0.011 | −0.011 | 0.014 | 0.043 | 0.035 |
| 350 | 530 | 0.009 | −0.009 | 0.013 | 0.036 | 0.029 |
| 350 | 540 | 0.008 | −0.007 | 0.012 | 0.028 | 0.026 |
| 350 | 550 | 0.008 | −0.006 | 0.009 | 0.022 | 0.023 |
| 350 | 560 | 0.006 | −0.004 | 0.007 | 0.017 | 0.016 |
| 350 | 570 | 0.006 | −0.003 | 0.006 | 0.013 | 0.012 |
| 350 | 580 | 0.005 | −0.003 | 0.004 | 0.010 | 0.007 |
| 350 | 590 | 0.004 | −0.002 | 0.002 | 0.008 | 0.004 |
| 350 | 600 | 0.004 | −0.001 | 0.001 | 0.007 | 0.003 |
| 350 | 610 | 0.004 | −0.001 | 0.000 | 0.006 | −0.001 |
| 350 | 620 | 0.003 | 0.000 | 0.000 | 0.005 | −0.005 |
| 350 | 630 | 0.003 | 0.001 | 0.000 | 0.005 | −0.004 |
| 350 | 640 | 0.003 | 0.001 | 0.000 | 0.004 | −0.007 |
| 350 | 650 | 0.003 | 0.001 | −0.001 | 0.004 | −0.008 |
| 350 | 660 | 0.002 | 0.001 | −0.001 | 0.004 | −0.009 |
| 360 | 390 | −0.005 | −0.002 | −0.004 | 0.012 | 0.131 |
| 360 | 400 | −0.008 | −0.012 | −0.025 | 0.033 | 0.051 |
| 360 | 410 | −0.016 | −0.016 | −0.058 | 0.025 | −0.019 |
| 360 | 420 | −0.021 | −0.012 | −0.026 | 0.007 | 0.093 |
| 360 | 430 | −0.013 | −0.025 | −0.017 | 0.059 | −0.039 |
| 360 | 440 | −0.010 | −0.021 | −0.009 | 0.051 | −0.010 |
| 360 | 450 | −0.001 | −0.024 | 0.024 | 0.062 | 0.035 |
| 360 | 460 | 0.007 | −0.028 | 0.032 | 0.079 | 0.002 |
| 360 | 470 | 0.010 | −0.022 | 0.030 | 0.067 | 0.015 |
| 360 | 480 | 0.012 | −0.018 | 0.034 | 0.061 | 0.043 |
| 360 | 490 | 0.014 | −0.017 | 0.031 | 0.063 | 0.050 |
| 360 | 500 | 0.014 | −0.014 | 0.023 | 0.060 | 0.054 |
| 360 | 510 | 0.013 | −0.011 | 0.018 | 0.050 | 0.064 |
| 360 | 520 | 0.012 | −0.009 | 0.015 | 0.042 | 0.062 |
| 360 | 530 | 0.011 | −0.007 | 0.013 | 0.034 | 0.058 |
| 360 | 540 | 0.010 | −0.006 | 0.010 | 0.026 | 0.050 |
| 360 | 550 | 0.008 | −0.004 | 0.007 | 0.020 | 0.045 |

-continued

| ex(nm) | em(nm) | evec3 | evec5 | evec10 | evec16 | evec18 |
|---|---|---|---|---|---|---|
| 360 | 560 | 0.007 | −0.003 | 0.005 | 0.015 | 0.034 |
| 360 | 570 | 0.006 | −0.002 | 0.004 | 0.011 | 0.027 |
| 360 | 580 | 0.006 | −0.001 | 0.001 | 0.008 | 0.022 |
| 360 | 590 | 0.005 | −0.001 | 0.000 | 0.005 | 0.015 |
| 360 | 600 | 0.004 | 0.000 | −0.001 | 0.004 | 0.010 |
| 360 | 610 | 0.004 | 0.001 | −0.002 | 0.005 | 0.006 |
| 360 | 620 | 0.003 | 0.001 | −0.001 | 0.004 | 0.002 |
| 360 | 630 | 0.003 | 0.002 | −0.001 | 0.004 | −0.001 |
| 360 | 640 | 0.003 | 0.002 | −0.001 | 0.004 | −0.003 |
| 360 | 650 | 0.003 | 0.002 | −0.002 | 0.005 | −0.005 |
| 360 | 660 | 0.003 | 0.002 | −0.002 | 0.004 | −0.006 |
| 360 | 670 | 0.002 | 0.002 | −0.002 | 0.005 | −0.008 |
| 360 | 680 | 0.002 | 0.002 | −0.002 | 0.004 | −0.007 |
| 370 | 400 | −0.007 | −0.011 | −0.031 | 0.021 | −0.018 |
| 370 | 410 | −0.017 | −0.013 | −0.073 | −0.002 | −0.093 |
| 370 | 420 | −0.024 | −0.005 | −0.039 | −0.038 | 0.052 |
| 370 | 430 | −0.016 | −0.021 | −0.024 | 0.022 | −0.085 |
| 370 | 440 | −0.014 | −0.016 | −0.010 | 0.010 | −0.044 |
| 370 | 450 | −0.004 | −0.020 | 0.030 | 0.026 | 0.005 |
| 370 | 460 | 0.007 | −0.026 | 0.042 | 0.056 | −0.023 |
| 370 | 470 | 0.010 | −0.020 | 0.041 | 0.047 | 0.002 |
| 370 | 480 | 0.012 | −0.016 | 0.044 | 0.044 | 0.038 |
| 370 | 490 | 0.015 | −0.015 | 0.039 | 0.051 | 0.046 |
| 370 | 500 | 0.015 | −0.012 | 0.029 | 0.049 | 0.058 |
| 370 | 510 | 0.014 | −0.009 | 0.023 | 0.042 | 0.074 |
| 370 | 520 | 0.013 | −0.007 | 0.017 | 0.033 | 0.073 |
| 370 | 530 | 0.011 | −0.005 | 0.013 | 0.026 | 0.068 |
| 370 | 540 | 0.010 | −0.003 | 0.009 | 0.018 | 0.061 |
| 370 | 550 | 0.009 | −0.001 | 0.005 | 0.014 | 0.053 |
| 370 | 560 | 0.008 | 0.000 | 0.002 | 0.008 | 0.045 |
| 370 | 570 | 0.007 | 0.000 | 0.001 | 0.006 | 0.038 |
| 370 | 580 | 0.006 | 0.001 | −0.002 | 0.003 | 0.028 |
| 370 | 590 | 0.005 | 0.001 | −0.002 | 0.001 | 0.023 |
| 370 | 600 | 0.004 | 0.002 | −0.003 | 0.002 | 0.017 |
| 370 | 610 | 0.004 | 0.002 | −0.003 | 0.002 | 0.011 |
| 370 | 620 | 0.004 | 0.003 | −0.004 | 0.001 | 0.007 |
| 370 | 630 | 0.004 | 0.002 | −0.004 | 0.002 | 0.002 |
| 370 | 640 | 0.003 | 0.003 | −0.003 | 0.002 | −0.003 |
| 370 | 650 | 0.003 | 0.003 | −0.003 | 0.002 | −0.003 |
| 370 | 660 | 0.003 | 0.003 | −0.003 | 0.003 | −0.005 |
| 370 | 670 | 0.002 | 0.003 | −0.003 | 0.003 | −0.006 |
| 370 | 680 | 0.002 | 0.003 | −0.003 | 0.003 | −0.006 |
| 370 | 690 | 0.002 | 0.003 | −0.003 | 0.003 | −0.007 |
| 380 | 410 | −0.017 | −0.003 | −0.088 | −0.035 | −0.123 |
| 380 | 420 | −0.026 | 0.008 | −0.053 | −0.089 | 0.040 |
| 380 | 430 | −0.017 | −0.010 | −0.034 | −0.030 | −0.080 |
| 380 | 440 | −0.017 | −0.002 | −0.021 | −0.049 | −0.043 |
| 380 | 450 | −0.007 | −0.008 | 0.028 | −0.028 | 0.004 |
| 380 | 460 | 0.005 | −0.017 | 0.044 | 0.012 | −0.023 |
| 380 | 470 | 0.008 | −0.011 | 0.042 | 0.008 | 0.002 |
| 380 | 480 | 0.011 | −0.008 | 0.047 | 0.012 | 0.033 |
| 380 | 490 | 0.014 | −0.009 | 0.045 | 0.025 | 0.040 |
| 380 | 500 | 0.014 | −0.007 | 0.031 | 0.025 | 0.058 |
| 380 | 510 | 0.013 | −0.004 | 0.024 | 0.020 | 0.071 |
| 380 | 520 | 0.012 | −0.003 | 0.019 | 0.017 | 0.074 |
| 380 | 530 | 0.011 | −0.002 | 0.014 | 0.013 | 0.070 |
| 380 | 540 | 0.010 | 0.000 | 0.009 | 0.007 | 0.063 |
| 380 | 550 | 0.008 | 0.001 | 0.005 | 0.002 | 0.056 |
| 380 | 560 | 0.007 | 0.002 | 0.002 | −0.001 | 0.048 |
| 380 | 570 | 0.006 | 0.003 | 0.000 | −0.003 | 0.040 |
| 380 | 580 | 0.005 | 0.003 | −0.002 | −0.004 | 0.031 |
| 380 | 590 | 0.005 | 0.003 | −0.004 | −0.005 | 0.026 |
| 380 | 600 | 0.004 | 0.003 | −0.004 | −0.004 | 0.019 |
| 380 | 610 | 0.004 | 0.003 | −0.005 | −0.002 | 0.013 |
| 380 | 620 | 0.003 | 0.003 | −0.005 | −0.002 | 0.008 |
| 380 | 630 | 0.003 | 0.003 | −0.004 | −0.002 | 0.003 |
| 380 | 640 | 0.003 | 0.003 | −0.004 | −0.001 | −0.001 |
| 380 | 650 | 0.003 | 0.003 | −0.003 | −0.001 | −0.005 |
| 380 | 660 | 0.002 | 0.003 | −0.004 | 0.000 | −0.004 |
| 380 | 670 | 0.002 | 0.003 | −0.003 | 0.001 | −0.006 |
| 380 | 680 | 0.002 | 0.003 | −0.002 | 0.001 | −0.007 |
| 380 | 690 | 0.002 | 0.003 | −0.003 | 0.001 | −0.007 |
| 390 | 420 | −0.026 | 0.019 | −0.054 | −0.118 | 0.022 |
| 390 | 430 | −0.016 | 0.001 | −0.031 | −0.069 | −0.063 |
| 390 | 440 | −0.017 | 0.009 | −0.016 | −0.094 | −0.027 |
| 390 | 450 | −0.008 | 0.004 | 0.029 | −0.074 | 0.006 |
| 390 | 460 | 0.004 | −0.006 | 0.047 | −0.030 | −0.025 |
| 390 | 470 | 0.006 | −0.001 | 0.047 | −0.029 | −0.005 |

| ex(nm) | em(nm) | evec3 | evec5 | evec10 | evec16 | evec18 |
|---|---|---|---|---|---|---|
| 390 | 480 | 0.009 | 0.001 | 0.050 | −0.022 | 0.017 |
| 390 | 490 | 0.012 | −0.001 | 0.045 | −0.005 | 0.029 |
| 390 | 500 | 0.012 | 0.000 | 0.034 | 0.000 | 0.040 |
| 390 | 510 | 0.012 | 0.001 | 0.026 | −0.002 | 0.055 |
| 390 | 520 | 0.011 | 0.002 | 0.020 | −0.004 | 0.059 |
| 390 | 530 | 0.010 | 0.003 | 0.015 | −0.005 | 0.058 |
| 390 | 540 | 0.008 | 0.004 | 0.010 | −0.009 | 0.053 |
| 390 | 550 | 0.007 | 0.005 | 0.006 | −0.011 | 0.048 |
| 390 | 560 | 0.006 | 0.005 | 0.002 | −0.012 | 0.043 |
| 390 | 570 | 0.005 | 0.005 | 0.000 | −0.012 | 0.036 |
| 390 | 580 | 0.005 | 0.005 | −0.002 | −0.013 | 0.030 |
| 390 | 590 | 0.004 | 0.004 | −0.003 | −0.012 | 0.025 |
| 390 | 600 | 0.004 | 0.004 | −0.004 | −0.010 | 0.020 |
| 390 | 610 | 0.003 | 0.004 | −0.005 | −0.009 | 0.016 |
| 390 | 620 | 0.003 | 0.004 | −0.004 | −0.006 | 0.011 |
| 390 | 630 | 0.003 | 0.004 | −0.004 | −0.005 | 0.002 |
| 390 | 640 | 0.003 | 0.004 | −0.003 | −0.003 | −0.001 |
| 390 | 650 | 0.003 | 0.004 | −0.002 | −0.003 | −0.004 |
| 390 | 660 | 0.002 | 0.004 | −0.003 | −0.002 | −0.004 |
| 390 | 670 | 0.002 | 0.003 | −0.003 | −0.001 | −0.005 |
| 390 | 680 | 0.002 | 0.003 | −0.002 | 0.000 | −0.006 |
| 390 | 690 | 0.002 | 0.004 | −0.003 | −0.001 | −0.004 |
| 400 | 430 | −0.018 | 0.017 | −0.038 | −0.099 | −0.028 |
| 400 | 440 | −0.020 | 0.024 | −0.024 | −0.130 | −0.003 |
| 400 | 450 | −0.012 | 0.017 | 0.020 | −0.112 | 0.018 |
| 400 | 460 | 0.000 | 0.008 | 0.038 | −0.068 | −0.011 |
| 400 | 470 | 0.003 | 0.011 | 0.038 | −0.063 | −0.001 |
| 400 | 480 | 0.006 | 0.011 | 0.042 | −0.052 | 0.018 |
| 400 | 490 | 0.009 | 0.008 | 0.040 | −0.033 | 0.026 |
| 400 | 500 | 0.010 | 0.008 | 0.030 | −0.024 | 0.041 |
| 400 | 510 | 0.010 | 0.009 | 0.023 | −0.024 | 0.054 |
| 400 | 520 | 0.009 | 0.008 | 0.017 | −0.022 | 0.061 |
| 400 | 530 | 0.008 | 0.008 | 0.013 | −0.022 | 0.058 |
| 400 | 540 | 0.007 | 0.008 | 0.009 | −0.024 | 0.055 |
| 400 | 550 | 0.006 | 0.008 | 0.005 | −0.024 | 0.054 |
| 400 | 560 | 0.005 | 0.008 | 0.002 | −0.023 | 0.045 |
| 400 | 570 | 0.004 | 0.008 | 0.000 | −0.021 | 0.039 |
| 400 | 580 | 0.004 | 0.007 | −0.002 | −0.021 | 0.035 |
| 400 | 590 | 0.003 | 0.006 | −0.003 | −0.019 | 0.029 |
| 400 | 600 | 0.003 | 0.006 | −0.004 | −0.016 | 0.024 |
| 400 | 610 | 0.002 | 0.005 | −0.004 | −0.013 | 0.019 |
| 400 | 620 | 0.003 | 0.005 | −0.004 | −0.012 | 0.012 |
| 400 | 630 | 0.002 | 0.005 | −0.002 | −0.009 | 0.007 |
| 400 | 640 | 0.003 | 0.004 | −0.002 | −0.008 | −0.002 |
| 400 | 650 | 0.003 | 0.005 | −0.004 | −0.005 | −0.002 |
| 400 | 660 | 0.002 | 0.004 | −0.001 | −0.004 | −0.003 |
| 400 | 670 | 0.002 | 0.004 | −0.002 | −0.002 | −0.004 |
| 400 | 680 | 0.002 | 0.004 | −0.002 | −0.002 | −0.005 |
| 400 | 690 | 0.002 | 0.004 | −0.003 | −0.001 | −0.005 |
| 410 | 440 | −0.020 | 0.035 | −0.003 | −0.141 | 0.070 |
| 410 | 450 | −0.013 | 0.029 | 0.031 | −0.129 | 0.039 |
| 410 | 460 | −0.002 | 0.019 | 0.050 | −0.087 | 0.006 |
| 410 | 470 | 0.001 | 0.022 | 0.047 | −0.082 | 0.000 |
| 410 | 480 | 0.005 | 0.021 | 0.047 | −0.068 | −0.004 |
| 410 | 490 | 0.008 | 0.017 | 0.042 | −0.046 | 0.003 |
| 410 | 500 | 0.009 | 0.016 | 0.033 | −0.037 | 0.019 |
| 410 | 510 | 0.009 | 0.016 | 0.025 | −0.034 | 0.033 |
| 410 | 520 | 0.008 | 0.015 | 0.019 | −0.031 | 0.040 |
| 410 | 530 | 0.007 | 0.014 | 0.013 | −0.030 | 0.043 |
| 410 | 540 | 0.006 | 0.013 | 0.009 | −0.031 | 0.043 |
| 410 | 550 | 0.005 | 0.012 | 0.005 | −0.029 | 0.041 |
| 410 | 560 | 0.005 | 0.012 | 0.003 | −0.029 | 0.038 |
| 410 | 570 | 0.004 | 0.010 | 0.001 | −0.027 | 0.030 |
| 410 | 580 | 0.003 | 0.009 | −0.001 | −0.025 | 0.029 |
| 410 | 590 | 0.003 | 0.008 | −0.002 | −0.022 | 0.022 |
| 410 | 600 | 0.002 | 0.007 | −0.003 | −0.019 | 0.020 |
| 410 | 610 | 0.002 | 0.006 | −0.003 | −0.017 | 0.015 |
| 410 | 620 | 0.002 | 0.006 | −0.003 | −0.014 | 0.011 |
| 410 | 630 | 0.002 | 0.005 | −0.003 | −0.011 | 0.004 |
| 410 | 640 | 0.002 | 0.005 | −0.002 | −0.010 | 0.001 |
| 410 | 650 | 0.002 | 0.005 | −0.002 | −0.007 | −0.001 |
| 410 | 660 | 0.002 | 0.004 | −0.002 | −0.006 | −0.004 |
| 410 | 670 | 0.002 | 0.004 | −0.002 | −0.004 | −0.004 |
| 410 | 680 | 0.002 | 0.004 | −0.002 | −0.002 | −0.005 |
| 410 | 690 | 0.002 | 0.004 | −0.002 | −0.003 | −0.005 |
| 420 | 450 | 0.001 | 0.013 | 0.052 | −0.056 | −0.036 |
| 420 | 460 | 0.008 | 0.013 | 0.060 | −0.043 | −0.063 |
| 420 | 470 | 0.011 | 0.017 | 0.058 | −0.039 | −0.074 |

| ex(nm) | em(nm) | evec3 | evec5 | evec10 | evec16 | evec18 |
|---|---|---|---|---|---|---|
| 420 | 480 | 0.013 | 0.019 | 0.051 | −0.035 | −0.073 |
| 420 | 490 | 0.015 | 0.020 | 0.041 | −0.026 | −0.056 |
| 420 | 500 | 0.015 | 0.021 | 0.029 | −0.020 | −0.031 |
| 420 | 510 | 0.014 | 0.021 | 0.020 | −0.019 | −0.012 |
| 420 | 520 | 0.012 | 0.021 | 0.012 | −0.021 | 0.007 |
| 420 | 530 | 0.011 | 0.020 | 0.008 | −0.025 | 0.015 |
| 420 | 540 | 0.009 | 0.019 | 0.003 | −0.027 | 0.021 |
| 420 | 550 | 0.008 | 0.018 | 0.000 | −0.028 | 0.023 |
| 420 | 560 | 0.007 | 0.017 | −0.003 | −0.028 | 0.022 |
| 420 | 570 | 0.006 | 0.015 | −0.004 | −0.028 | 0.020 |
| 420 | 580 | 0.005 | 0.013 | −0.005 | −0.026 | 0.018 |
| 420 | 590 | 0.004 | 0.012 | −0.006 | −0.022 | 0.017 |
| 420 | 600 | 0.003 | 0.010 | −0.007 | −0.021 | 0.015 |
| 420 | 610 | 0.003 | 0.009 | −0.006 | −0.018 | 0.012 |
| 420 | 620 | 0.003 | 0.008 | −0.006 | −0.016 | 0.009 |
| 420 | 630 | 0.002 | 0.007 | −0.005 | −0.012 | 0.005 |
| 420 | 640 | 0.003 | 0.006 | −0.003 | −0.010 | 0.001 |
| 420 | 650 | 0.002 | 0.006 | −0.003 | −0.007 | 0.000 |
| 420 | 660 | 0.002 | 0.005 | −0.003 | −0.006 | −0.002 |
| 420 | 670 | 0.002 | 0.005 | −0.003 | −0.005 | −0.003 |
| 420 | 680 | 0.002 | 0.004 | −0.003 | −0.004 | −0.003 |
| 420 | 690 | 0.001 | 0.004 | −0.003 | −0.002 | −0.005 |
| 430 | 460 | 0.013 | 0.010 | 0.050 | −0.012 | −0.121 |
| 430 | 470 | 0.017 | 0.017 | 0.046 | −0.010 | −0.143 |
| 430 | 480 | 0.019 | 0.022 | 0.038 | −0.006 | −0.136 |
| 430 | 490 | 0.020 | 0.025 | 0.025 | −0.001 | −0.115 |
| 430 | 500 | 0.020 | 0.027 | 0.012 | 0.003 | −0.089 |
| 430 | 510 | 0.019 | 0.028 | 0.004 | 0.001 | −0.064 |
| 430 | 520 | 0.018 | 0.028 | −0.003 | −0.004 | −0.040 |
| 430 | 530 | 0.015 | 0.027 | −0.008 | −0.009 | −0.024 |
| 430 | 540 | 0.013 | 0.027 | −0.011 | −0.014 | −0.016 |
| 430 | 550 | 0.012 | 0.025 | −0.014 | −0.016 | −0.004 |
| 430 | 560 | 0.010 | 0.023 | −0.016 | −0.018 | −0.003 |
| 430 | 570 | 0.009 | 0.021 | −0.017 | −0.017 | −0.003 |
| 430 | 580 | 0.007 | 0.018 | −0.016 | −0.018 | 0.002 |
| 430 | 590 | 0.006 | 0.016 | −0.016 | −0.016 | 0.002 |
| 430 | 600 | 0.005 | 0.014 | −0.015 | −0.015 | 0.003 |
| 430 | 610 | 0.005 | 0.013 | −0.015 | −0.012 | 0.003 |
| 430 | 620 | 0.004 | 0.011 | −0.013 | −0.011 | 0.001 |
| 430 | 630 | 0.004 | 0.010 | −0.012 | −0.007 | 0.000 |
| 430 | 640 | 0.003 | 0.009 | −0.009 | −0.006 | −0.003 |
| 430 | 650 | 0.003 | 0.007 | −0.009 | −0.004 | −0.004 |
| 430 | 660 | 0.003 | 0.007 | −0.008 | −0.002 | −0.006 |
| 430 | 670 | 0.003 | 0.006 | −0.007 | −0.002 | −0.005 |
| 430 | 680 | 0.002 | 0.005 | −0.006 | 0.001 | −0.006 |
| 430 | 690 | 0.002 | 0.005 | −0.006 | 0.000 | −0.006 |
| 440 | 470 | 0.014 | 0.018 | 0.025 | 0.000 | −0.127 |
| 440 | 480 | 0.018 | 0.023 | 0.016 | 0.006 | −0.131 |
| 440 | 490 | 0.020 | 0.027 | 0.005 | 0.013 | −0.116 |
| 440 | 500 | 0.020 | 0.030 | −0.005 | 0.018 | −0.094 |
| 440 | 510 | 0.020 | 0.032 | −0.012 | 0.017 | −0.079 |
| 440 | 520 | 0.019 | 0.032 | −0.019 | 0.013 | −0.056 |
| 440 | 530 | 0.017 | 0.032 | −0.022 | 0.006 | −0.040 |
| 440 | 540 | 0.015 | 0.031 | −0.023 | 0.000 | −0.029 |
| 440 | 550 | 0.014 | 0.029 | −0.024 | −0.002 | −0.022 |
| 440 | 560 | 0.012 | 0.027 | −0.026 | −0.006 | −0.017 |
| 440 | 570 | 0.011 | 0.024 | −0.024 | −0.007 | −0.016 |
| 440 | 580 | 0.009 | 0.022 | −0.024 | −0.006 | −0.012 |
| 440 | 590 | 0.008 | 0.019 | −0.022 | −0.005 | −0.010 |
| 440 | 600 | 0.007 | 0.017 | −0.022 | −0.003 | −0.004 |
| 440 | 610 | 0.006 | 0.015 | −0.020 | −0.003 | −0.004 |
| 440 | 620 | 0.005 | 0.013 | −0.017 | −0.001 | −0.004 |
| 440 | 630 | 0.005 | 0.012 | −0.017 | 0.000 | −0.003 |
| 440 | 640 | 0.004 | 0.010 | −0.014 | 0.002 | −0.003 |
| 440 | 650 | 0.004 | 0.008 | −0.013 | 0.003 | −0.003 |
| 440 | 660 | 0.003 | 0.008 | −0.011 | 0.004 | −0.002 |
| 440 | 670 | 0.003 | 0.007 | −0.010 | 0.004 | −0.004 |
| 440 | 680 | 0.003 | 0.007 | −0.010 | 0.005 | −0.002 |
| 440 | 690 | 0.002 | 0.006 | −0.009 | 0.005 | −0.002 |
| 450 | 480 | 0.013 | 0.021 | −0.001 | 0.009 | −0.082 |
| 450 | 490 | 0.016 | 0.026 | −0.010 | 0.017 | −0.079 |
| 450 | 500 | 0.018 | 0.030 | −0.019 | 0.024 | −0.067 |
| 450 | 510 | 0.019 | 0.033 | −0.025 | 0.025 | −0.055 |
| 450 | 520 | 0.018 | 0.035 | −0.028 | 0.020 | −0.045 |
| 450 | 530 | 0.017 | 0.035 | −0.029 | 0.013 | −0.035 |
| 450 | 540 | 0.015 | 0.034 | −0.031 | 0.007 | −0.024 |
| 450 | 550 | 0.014 | 0.033 | −0.032 | 0.003 | −0.019 |
| 450 | 560 | 0.013 | 0.031 | −0.031 | 0.002 | −0.017 |
| 450 | 570 | 0.011 | 0.028 | −0.030 | 0.001 | −0.015 |
| 450 | 580 | 0.010 | 0.025 | −0.029 | 0.000 | −0.012 |
| 450 | 590 | 0.009 | 0.022 | −0.028 | 0.001 | −0.009 |
| 450 | 600 | 0.008 | 0.020 | −0.026 | 0.002 | −0.007 |
| 450 | 610 | 0.007 | 0.017 | −0.024 | 0.003 | −0.006 |
| 450 | 620 | 0.006 | 0.015 | −0.022 | 0.004 | −0.004 |
| 450 | 630 | 0.005 | 0.013 | −0.021 | 0.005 | −0.001 |
| 450 | 640 | 0.004 | 0.011 | −0.018 | 0.006 | −0.003 |
| 450 | 650 | 0.004 | 0.010 | −0.016 | 0.005 | −0.003 |
| 450 | 660 | 0.003 | 0.009 | −0.014 | 0.006 | −0.004 |
| 450 | 670 | 0.003 | 0.008 | −0.012 | 0.007 | −0.003 |
| 450 | 680 | 0.003 | 0.007 | −0.011 | 0.007 | −0.004 |
| 450 | 690 | 0.002 | 0.006 | −0.010 | 0.006 | −0.003 |
| 460 | 490 | 0.013 | 0.023 | −0.024 | 0.024 | −0.050 |
| 460 | 500 | 0.015 | 0.028 | −0.033 | 0.032 | −0.049 |
| 460 | 510 | 0.017 | 0.033 | −0.039 | 0.035 | −0.044 |
| 460 | 520 | 0.017 | 0.035 | −0.042 | 0.030 | −0.039 |
| 460 | 530 | 0.016 | 0.037 | −0.044 | 0.022 | −0.034 |
| 460 | 540 | 0.016 | 0.037 | −0.045 | 0.017 | −0.027 |
| 460 | 550 | 0.015 | 0.035 | −0.045 | 0.014 | −0.025 |
| 460 | 560 | 0.014 | 0.034 | −0.044 | 0.012 | −0.022 |
| 460 | 570 | 0.012 | 0.031 | −0.043 | 0.011 | −0.023 |
| 460 | 580 | 0.011 | 0.028 | −0.042 | 0.010 | −0.021 |
| 460 | 590 | 0.010 | 0.025 | −0.039 | 0.011 | −0.018 |
| 460 | 600 | 0.009 | 0.022 | −0.037 | 0.012 | −0.013 |
| 460 | 610 | 0.008 | 0.020 | −0.035 | 0.013 | −0.011 |
| 460 | 620 | 0.007 | 0.017 | −0.031 | 0.013 | −0.006 |
| 460 | 630 | 0.006 | 0.015 | −0.028 | 0.014 | −0.008 |
| 460 | 640 | 0.005 | 0.013 | −0.025 | 0.013 | −0.007 |
| 460 | 650 | 0.005 | 0.011 | −0.022 | 0.012 | −0.006 |
| 460 | 660 | 0.004 | 0.010 | −0.020 | 0.012 | −0.003 |
| 460 | 670 | 0.004 | 0.009 | −0.018 | 0.011 | −0.008 |
| 460 | 680 | 0.003 | 0.008 | −0.016 | 0.011 | −0.004 |
| 460 | 690 | 0.002 | 0.007 | −0.012 | 0.009 | 0.004 |
| 470 | 500 | 0.011 | 0.024 | −0.029 | 0.025 | −0.007 |
| 470 | 510 | 0.012 | 0.030 | −0.034 | 0.025 | −0.005 |
| 470 | 520 | 0.013 | 0.035 | −0.039 | 0.021 | −0.002 |
| 470 | 530 | 0.013 | 0.037 | −0.040 | 0.013 | 0.003 |
| 470 | 540 | 0.013 | 0.038 | −0.042 | 0.008 | 0.003 |
| 470 | 550 | 0.012 | 0.038 | −0.042 | 0.006 | 0.002 |
| 470 | 560 | 0.012 | 0.036 | −0.043 | 0.006 | 0.001 |
| 470 | 570 | 0.011 | 0.034 | −0.043 | 0.006 | −0.002 |
| 470 | 580 | 0.010 | 0.031 | −0.041 | 0.007 | −0.001 |
| 470 | 590 | 0.009 | 0.028 | −0.040 | 0.009 | −0.002 |
| 470 | 600 | 0.009 | 0.025 | −0.038 | 0.011 | 0.001 |
| 470 | 610 | 0.008 | 0.023 | −0.035 | 0.014 | 0.002 |
| 470 | 620 | 0.007 | 0.020 | −0.033 | 0.014 | 0.002 |
| 470 | 630 | 0.006 | 0.017 | −0.029 | 0.015 | 0.003 |
| 470 | 640 | 0.005 | 0.015 | −0.027 | 0.016 | 0.001 |
| 470 | 650 | 0.005 | 0.013 | −0.024 | 0.016 | −0.001 |
| 470 | 660 | 0.004 | 0.011 | −0.021 | 0.015 | 0.003 |
| 470 | 670 | 0.004 | 0.010 | −0.019 | 0.013 | 0.000 |
| 470 | 680 | 0.003 | 0.009 | −0.016 | 0.012 | 0.000 |
| 470 | 690 | 0.003 | 0.007 | −0.014 | 0.012 | −0.002 |
| 480 | 510 | 0.009 | 0.024 | −0.031 | 0.024 | −0.003 |
| 480 | 520 | 0.010 | 0.031 | −0.037 | 0.017 | −0.005 |
| 480 | 530 | 0.011 | 0.036 | −0.040 | 0.011 | −0.007 |
| 480 | 540 | 0.011 | 0.038 | −0.043 | 0.005 | −0.009 |
| 480 | 550 | 0.011 | 0.038 | −0.046 | 0.006 | −0.010 |
| 480 | 560 | 0.011 | 0.038 | −0.047 | 0.008 | −0.013 |
| 480 | 570 | 0.011 | 0.036 | −0.047 | 0.008 | −0.014 |
| 480 | 580 | 0.010 | 0.033 | −0.046 | 0.010 | −0.016 |
| 480 | 590 | 0.010 | 0.030 | −0.046 | 0.014 | −0.011 |
| 480 | 600 | 0.009 | 0.028 | −0.043 | 0.018 | −0.011 |
| 480 | 610 | 0.008 | 0.025 | −0.041 | 0.020 | −0.011 |
| 480 | 620 | 0.008 | 0.022 | −0.038 | 0.022 | −0.009 |
| 480 | 630 | 0.007 | 0.019 | −0.034 | 0.022 | −0.007 |
| 480 | 640 | 0.006 | 0.017 | −0.031 | 0.022 | −0.006 |
| 480 | 650 | 0.005 | 0.015 | −0.028 | 0.020 | −0.005 |
| 480 | 660 | 0.005 | 0.012 | −0.025 | 0.020 | −0.005 |
| 480 | 670 | 0.004 | 0.011 | −0.022 | 0.018 | −0.003 |
| 480 | 680 | 0.004 | 0.010 | −0.018 | 0.015 | −0.004 |
| 480 | 690 | 0.003 | 0.009 | −0.017 | 0.015 | −0.003 |
| 490 | 520 | 0.006 | 0.026 | −0.031 | 0.008 | 0.010 |
| 490 | 530 | 0.007 | 0.033 | −0.036 | −0.001 | 0.010 |
| 490 | 540 | 0.008 | 0.037 | −0.040 | −0.005 | 0.005 |
| 490 | 550 | 0.008 | 0.039 | −0.045 | −0.003 | 0.004 |
| 490 | 560 | 0.009 | 0.038 | −0.048 | 0.001 | 0.000 |

-continued

| ex(nm) | em(nm) | evec3 | evec5 | evec10 | evec16 | evec18 |
|---|---|---|---|---|---|---|
| 490 | 570 | 0.009 | 0.037 | −0.050 | 0.004 | −0.006 |
| 490 | 580 | 0.009 | 0.034 | −0.049 | 0.009 | −0.006 |
| 490 | 590 | 0.009 | 0.032 | −0.048 | 0.012 | −0.006 |
| 490 | 600 | 0.008 | 0.029 | −0.047 | 0.017 | −0.007 |
| 490 | 610 | 0.008 | 0.026 | −0.046 | 0.022 | −0.004 |
| 490 | 620 | 0.007 | 0.023 | −0.042 | 0.023 | −0.004 |
| 490 | 630 | 0.007 | 0.021 | −0.039 | 0.024 | −0.003 |
| 490 | 640 | 0.006 | 0.018 | −0.035 | 0.025 | −0.003 |
| 490 | 650 | 0.006 | 0.016 | −0.032 | 0.024 | −0.003 |
| 490 | 660 | 0.005 | 0.014 | −0.029 | 0.023 | −0.001 |
| 490 | 670 | 0.004 | 0.012 | −0.027 | 0.023 | −0.001 |
| 490 | 680 | 0.004 | 0.011 | −0.021 | 0.019 | −0.002 |
| 490 | 690 | 0.004 | 0.010 | −0.021 | 0.019 | −0.001 |
| 500 | 530 | 0.002 | 0.030 | −0.024 | −0.017 | 0.026 |
| 500 | 540 | 0.004 | 0.035 | −0.029 | −0.022 | 0.026 |
| 500 | 550 | 0.005 | 0.038 | −0.035 | −0.020 | 0.021 |
| 500 | 560 | 0.006 | 0.038 | −0.041 | −0.014 | 0.015 |
| 500 | 570 | 0.007 | 0.038 | −0.044 | −0.010 | 0.012 |
| 500 | 580 | 0.007 | 0.035 | −0.044 | −0.003 | 0.009 |
| 500 | 590 | 0.007 | 0.033 | −0.044 | 0.004 | 0.008 |
| 500 | 600 | 0.007 | 0.030 | −0.044 | 0.010 | 0.007 |
| 500 | 610 | 0.007 | 0.028 | −0.043 | 0.014 | 0.010 |
| 500 | 620 | 0.006 | 0.025 | −0.041 | 0.020 | 0.007 |
| 500 | 630 | 0.006 | 0.022 | −0.040 | 0.021 | 0.007 |
| 500 | 640 | 0.006 | 0.020 | −0.036 | 0.022 | 0.007 |
| 500 | 650 | 0.005 | 0.017 | −0.033 | 0.025 | 0.006 |
| 500 | 660 | 0.005 | 0.016 | −0.030 | 0.022 | 0.007 |
| 500 | 670 | 0.004 | 0.014 | −0.027 | 0.020 | 0.003 |
| 500 | 680 | 0.004 | 0.011 | −0.024 | 0.021 | 0.000 |
| 500 | 690 | 0.004 | 0.011 | −0.022 | 0.020 | 0.002 |
| 510 | 540 | 0.000 | 0.032 | −0.022 | −0.036 | 0.036 |
| 510 | 550 | 0.002 | 0.036 | −0.029 | −0.032 | 0.034 |
| 510 | 560 | 0.003 | 0.037 | −0.036 | −0.027 | 0.026 |
| 510 | 570 | 0.005 | 0.037 | −0.042 | −0.018 | 0.022 |
| 510 | 580 | 0.005 | 0.035 | −0.044 | −0.010 | 0.017 |
| 510 | 590 | 0.005 | 0.033 | −0.043 | −0.003 | 0.010 |
| 510 | 600 | 0.006 | 0.030 | −0.043 | 0.005 | 0.013 |
| 510 | 610 | 0.006 | 0.028 | −0.043 | 0.012 | 0.008 |
| 510 | 620 | 0.006 | 0.025 | −0.041 | 0.017 | 0.011 |
| 510 | 630 | 0.006 | 0.023 | −0.038 | 0.019 | 0.008 |
| 510 | 640 | 0.006 | 0.020 | −0.037 | 0.023 | 0.008 |
| 510 | 650 | 0.005 | 0.018 | −0.034 | 0.025 | 0.006 |
| 510 | 660 | 0.005 | 0.016 | −0.029 | 0.022 | 0.001 |
| 510 | 670 | 0.004 | 0.014 | −0.028 | 0.022 | 0.005 |
| 510 | 680 | 0.004 | 0.013 | −0.024 | 0.020 | 0.005 |
| 510 | 690 | 0.003 | 0.012 | −0.021 | 0.019 | 0.006 |
| 520 | 550 | −0.001 | 0.033 | −0.024 | −0.040 | 0.042 |
| 520 | 560 | 0.001 | 0.035 | −0.032 | −0.031 | 0.033 |
| 520 | 570 | 0.003 | 0.037 | −0.039 | −0.024 | 0.027 |
| 520 | 580 | 0.004 | 0.035 | −0.041 | −0.017 | 0.019 |
| 520 | 590 | 0.004 | 0.033 | −0.041 | −0.009 | 0.017 |
| 520 | 600 | 0.005 | 0.030 | −0.042 | −0.004 | 0.013 |
| 520 | 610 | 0.005 | 0.028 | −0.041 | 0.005 | 0.012 |
| 520 | 620 | 0.005 | 0.026 | −0.040 | 0.011 | 0.011 |
| 520 | 630 | 0.005 | 0.023 | −0.038 | 0.016 | 0.007 |
| 520 | 640 | 0.005 | 0.021 | −0.037 | 0.018 | 0.007 |
| 520 | 650 | 0.005 | 0.019 | −0.034 | 0.023 | 0.006 |
| 520 | 660 | 0.005 | 0.017 | −0.032 | 0.021 | 0.005 |
| 520 | 670 | 0.004 | 0.015 | −0.029 | 0.021 | 0.003 |
| 520 | 680 | 0.004 | 0.014 | −0.028 | 0.021 | 0.004 |
| 520 | 690 | 0.004 | 0.013 | −0.025 | 0.017 | 0.005 |
| 530 | 560 | 0.000 | 0.032 | −0.030 | −0.032 | 0.040 |
| 530 | 570 | 0.002 | 0.033 | −0.035 | −0.024 | 0.030 |
| 530 | 580 | 0.003 | 0.032 | −0.037 | −0.018 | 0.022 |
| 530 | 590 | 0.003 | 0.030 | −0.037 | −0.013 | 0.015 |
| 530 | 600 | 0.004 | 0.029 | −0.038 | −0.004 | 0.012 |
| 530 | 610 | 0.004 | 0.027 | −0.038 | 0.003 | 0.010 |
| 530 | 620 | 0.005 | 0.025 | −0.038 | 0.011 | 0.009 |
| 530 | 630 | 0.005 | 0.023 | −0.037 | 0.015 | 0.011 |
| 530 | 640 | 0.005 | 0.021 | −0.034 | 0.019 | 0.005 |
| 530 | 650 | 0.005 | 0.019 | −0.033 | 0.022 | 0.003 |
| 530 | 660 | 0.004 | 0.017 | −0.031 | 0.020 | 0.003 |
| 530 | 670 | 0.004 | 0.015 | −0.026 | 0.021 | 0.000 |
| 530 | 680 | 0.004 | 0.013 | −0.024 | 0.023 | −0.001 |
| 530 | 690 | 0.004 | 0.015 | −0.025 | 0.021 | 0.007 |
| 540 | 570 | 0.003 | 0.029 | −0.038 | −0.012 | 0.031 |
| 540 | 580 | 0.003 | 0.028 | −0.038 | −0.009 | 0.019 |
| 540 | 590 | 0.004 | 0.027 | −0.037 | −0.007 | 0.015 |
| 540 | 600 | 0.004 | 0.026 | −0.036 | 0.000 | 0.011 |
| 540 | 610 | 0.004 | 0.025 | −0.038 | 0.006 | 0.010 |
| 540 | 620 | 0.005 | 0.024 | −0.036 | 0.012 | 0.007 |
| 540 | 630 | 0.005 | 0.022 | −0.035 | 0.015 | 0.005 |
| 540 | 640 | 0.005 | 0.020 | −0.033 | 0.020 | 0.006 |
| 540 | 650 | 0.005 | 0.018 | −0.031 | 0.021 | −0.001 |
| 540 | 660 | 0.005 | 0.017 | −0.031 | 0.022 | 0.004 |
| 540 | 670 | 0.004 | 0.015 | −0.027 | 0.024 | 0.001 |
| 540 | 680 | 0.004 | 0.015 | −0.025 | 0.022 | 0.001 |
| 540 | 690 | 0.004 | 0.013 | −0.025 | 0.021 | 0.004 |
| 550 | 580 | 0.005 | 0.025 | −0.043 | 0.005 | 0.021 |
| 550 | 590 | 0.004 | 0.023 | −0.038 | 0.005 | 0.014 |
| 550 | 600 | 0.005 | 0.024 | −0.036 | 0.010 | 0.013 |
| 550 | 610 | 0.005 | 0.023 | −0.037 | 0.011 | 0.011 |
| 550 | 620 | 0.005 | 0.022 | −0.037 | 0.018 | 0.011 |
| 550 | 630 | 0.005 | 0.021 | −0.036 | 0.020 | 0.008 |
| 550 | 640 | 0.005 | 0.019 | −0.034 | 0.024 | 0.005 |
| 550 | 650 | 0.005 | 0.018 | −0.032 | 0.025 | 0.006 |
| 550 | 660 | 0.005 | 0.017 | −0.031 | 0.025 | 0.005 |
| 550 | 670 | 0.005 | 0.015 | −0.027 | 0.025 | 0.002 |
| 550 | 680 | 0.004 | 0.015 | −0.025 | 0.025 | 0.004 |
| 550 | 690 | 0.004 | 0.015 | −0.025 | 0.024 | 0.006 |

APPENDIX III: REFERENCES

The disclosures of the following publications, patents and applications are expressly incorporated herein by reference, as are any of the other references mentioned above:

A two-stage fluorescence diagnostic method is disclosed in detail in application Ser. No. 08/060,432, filed May 12, 1993, and is assigned to the same assignee as the present invention.

An application entitled "Optical Method And apparatus for the Diagnosis of Cervical Precancers using Raman and Fluorescence Spectroscopies" (Richards-Kortum et al.) was filed on Mar. 14, 1995, and is assigned to the same assignee as the present invention.

Lui et al., "Fluorescence and Time-Resolved Light Scattering as Optical Diagnostic Techniques to Separate Diseased and Normal Biomedical Media," J. Photochem. Photobiol. B: Biol. 16, 187–209, 1992.

Wong et al., "Infrared Spectroscopy of Human Cervical Cells: Evidence of Extensive Structural Changes during Carcinogenesis", Proc. Nat'l Acad. Sci. USA, 88, 10988–10992, 1991.

Kurman RJ, Henson DE, Herbst AL, Noller KL, Shiffman MH, "Interim guidelines for management of abnormal cervical cytology," JAMA, 271, 1866–1869, 1994.

Davison JM, Marty JJ, "Detecting premalignant cervical lesions: Contributions of screening colposcopy to cytology," J Reproductive Medicine, 39, 388–392, 1994.

Banda-Gamboa, Hugo, et al, "Automation in cervical cytology: an overview," Anal Cell Path, 4 (1992) 25–48.

Chance B, Thorell L, "Localization and kinetics of reduced PN in living cells by microfluorimetry," J Biol Chem 234:3044, 1959.

Caspersson TC, Cell Structure and Function, ch 4, Norton & Co, New York, 1950.

Aubin JE, "Autofluorescence of Viable Cultured Mammalian Cells," J Histochem Cytochem, 27(1), 36–43, 1979.

Benson RC, et al, "Cellular Autofluorescence: Is It Due to Flavins?" J Histochem Cytochem, 27 (1), 44–48, 1979.

Tamura M, . . . Chance B, "In Vivo Study of Tissue Oxygen . . . " Annu Rev Physiol, 1989, 51:813–814.

Hutchinson, ML, Agarwal, P, Denault, T, Berger, B, Cibas, ES, "A New Look at Cervical Cytology," *Acta Cytologica*, 36, 4: 499–504, 1992.

Taylor DG, Demas JN, "Light intensity measurements I: Large area bolometers with uW sensitivities and absolute calibration of the rhodamine B quantum counter," *Anal Chem*, 51, 712–717, 1979.

Vooijs GP, "Benign proliferative reactions, intraepithelial neoplasia and invasive cancer of the uterine cervix," in Bibbo M (ed), *Comprehensive Cytopathology*, WB Saunders Company, pp 176–177, 1991.

Dillon WR and Goldstein M, "Multivariate Analysis Methods and Applications," Chapter 10. Wiley & Sons, New York (1985)

What is claimed is:

1. A method of detecting tissue abnormality in a tissue sample in vitro comprising:
   (i) providing a tissue sample;
   (ii) sequentially illuminating said tissue sample in vitro with a set of at least two electromagnetic radiation wavelengths selected to cause said tissue sample to produce a set of fluorescence intensity spectra indicative of tissue abnormality;
   (iii) detecting said set of fluorescence intensity spectra emitted from said tissue sample as a result of illumination with each of said wavelengths; and
   (iv) calculating from said set of fluorescence intensity spectra, a probability that said tissue sample is normal or abnormal.

2. The method of claim 1, wherein said calculating step comprises, conducting principal component analysis of said fluorescent spectra relative to a set of preprocessed spectra obtained from tissue samples of known pathology.

3. The method of claim 2, wherein said principal component analysis does not include the highest and lowest order principal components.

4. The method of claim 3, wherein said principal component analysis comprises a Fisher's determinant analysis.

5. The method of claim 1, wherein said calculating step comprises, normalizing said spectra relative to a maximum intensity within said spectra.

6. The method of claim 5, wherein said calculating step further comprises, mean-scaling said spectra as a function of a mean intensity of spectra.

7. The method of claim 1, wherein said providing step comprises obtaining said tissue sample by biopsy.

8. The method of claim 7, wherein said providing step further comprises ethanol fixation of said tissue sample.

9. The method of claim 8, wherein said providing step even further comprises generating a monolayer cell touch preparation or a pellet.

10. The method of claim 1, wherein said set of at least two electromagnetic wavelengths are 250 nm, 550 nm and all wavelengths between 250 nm and 550 nm at 10 nm intervals.

11. The method of claim 1, wherein said detecting step comprises, detecting an intensity of fluorescence at 250 nm, 700 nm and all wavelengths between 250 nm and 700 nm at 10 nm intervals.

12. The method of claim 1, wherein said illuminating comprises, illuminating said sample substantially normal to a surface of said sample, and wherein said detecting step comprises, detecting said spectra at an angle of approximately 20° from normal.

13. The method of claim 1, wherein at least 10 sequential electromagnetic radiation wavelengths are used in said illuminating step to produce a set of at least 10 different fluorescence intensity spectra in said detecting step, each spectra comprising fluorescence intensity at at least 11 wavelengths.

14. The method of claim 13, wherein at least 30 sequential electromagnetic radiation wavelengths are used in said illuminating step to produce a set of at least 30 different fluorescence intensity spectra in said detecting step, each spectra comprising fluorescence intensity at at least 31 wavelengths.

15. The method of claim 14, wherein at least 50 sequential electromagnetic radiation wavelengths are used in said illuminating step to produce a set of at least 50 different fluorescence intensity spectra in said detecting step, each said spectra comprising fluorescence intensity at at least 51 wavelengths.

* * * * *

UNITED STATES PATENT AND TRADEMARK OFFICE
CERTIFICATE OF CORRECTION

PATENT NO.    :   5,612,540

DATED         :   March 18, 1997

INVENTOR(S)   :   Richards-Kortum et al.

It is certified that error appears in the above-identified patent and that said Letters Patent is hereby corrected as shown below:

On the title page, at item [56] after U.S. PATENT DOCUMENTS please insert
-- 5,003,977     4/1991 Suzuki et al.
    5,293,872     3/1994 Alfano et al.
    5,348,003     9/1994 Caro
    5,450,857     9/1995 Garfield et al.--.

On the title page, at item [56] after FOREIGN PATENT DOCUMENTS please insert
-- 0 359 433     3/1990    EPO
    0 650 694     5/1995    EPO
    WO 90/06718    6/1990    WIPO
    WO 90/12536    11/1990    WIPO
    WO 92/15008    9/1992    WIPO
    WO 93/03672    3/1993    WIPO
    WO 94/26168    11/1994    WIPO --.

On title page, at item [56] after OTHER PUBLICATIONS please insert
-- International Search Report dated July 17, 1996
   International Search Report dated July 12, 1996
   International Search Report dated July 12, 1996 --.

Signed and Sealed this

Twenty-fourth Day of June, 1997

Attest:

BRUCE LEHMAN

*Attesting Officer*      *Commissioner of Patents and Trademarks*